US009265490B2

(12) United States Patent
Bowman et al.

(10) Patent No.: US 9,265,490 B2
(45) Date of Patent: Feb. 23, 2016

(54) DETACHABLE DILATOR BLADE

(75) Inventors: Brian Scott Bowman, San Diego, CA (US); Corbett Stone, San Diego, CA (US); Benjamin Arnold, San Diego, CA (US); Kabir Gambhir, San Diego, CA (US); Robert J. Bishop, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 792 days.

(21) Appl. No.: 13/447,931

(22) Filed: Apr. 16, 2012

(65) Prior Publication Data

US 2013/0274557 A1 Oct. 17, 2013

(51) Int. Cl.
*A61B 1/32* (2006.01)
*A61B 17/02* (2006.01)
*A61B 5/0488* (2006.01)
*A61M 29/00* (2006.01)
*A61B 17/00* (2006.01)

(52) U.S. Cl.
CPC ........... *A61B 17/0206* (2013.01); *A61B 17/025* (2013.01); *A61B 5/0488* (2013.01); *A61B 2017/00039* (2013.01); *A61B 2017/0262* (2013.01); *A61M 29/00* (2013.01)

(58) Field of Classification Search
CPC ............... A61B 17/02; A61B 17/0206; A61B 17/0218; A61B 17/025; A61B 17/0256; A61B 17/0293; A61B 17/7076; A61B 1/32
See application file for complete search history.

(56) References Cited

U.S. PATENT DOCUMENTS

| | | | |
|---|---|---|---|
| 5,503,617 A | 4/1996 | Jako | |
| 5,964,698 A | 10/1999 | Fowler | |
| 6,709,389 B2 | 3/2004 | Farascioni | |
| 6,932,765 B2 | 8/2005 | Berg | |
| 7,108,698 B2 | 9/2006 | Robbins et al. | |
| 7,226,413 B2 | 6/2007 | McKinley | |
| 7,435,219 B2 * | 10/2008 | Kim .............................. | 600/233 |
| 7,481,766 B2 | 1/2009 | Lee et al. | |

(Continued)

FOREIGN PATENT DOCUMENTS

EP  0792620  9/1997
EP  2179695  4/2010

(Continued)

OTHER PUBLICATIONS

European Patent Application No. 13163266.3: Partial Search Report dated Jul. 12, 2013, 8 pages.

(Continued)

*Primary Examiner* — Mary Hoffman
(74) *Attorney, Agent, or Firm* — Baker & Hostetler LLP

(57) ABSTRACT

A tissue retraction system includes a dilator and a first retractor member and a retraction assembly. The dilator is configured to be inserted into a tissue body and also includes at least one engagement member. The first retractor member includes a body and at least one engagement member that is configured to attach to the at least one engagement member of the dilator so as to removably attach the retractor member to the dilator body. The retraction assembly includes a retractor body and at least a second retractor member that is movably supported by the retractor body. The retractor body is configured to be attached to the first retractor member. The tissue protection system may also include a neuromonitoring member configured to determine a characteristics of the tissue.

20 Claims, 26 Drawing Sheets

(56) References Cited

U.S. PATENT DOCUMENTS

| | | | |
|---|---|---|---|
| 7,494,463 B2 | 2/2009 | Nehls | |
| 7,582,058 B1 * | 9/2009 | Miles et al. | 600/202 |
| 7,691,057 B2 | 4/2010 | Miles et al. | |
| 7,785,253 B1 | 8/2010 | Arambula et al. | |
| 7,935,051 B2 | 5/2011 | Miles et al. | |
| RE42,525 E * | 7/2011 | Simonson | 604/117 |
| 8,005,535 B2 | 8/2011 | Gharib et al. | |
| 8,027,716 B2 | 9/2011 | Gharib et al. | |
| 8,114,019 B2 | 2/2012 | Miles et al. | |
| 8,313,430 B1 * | 11/2012 | Pimenta | 600/202 |
| 2004/0225196 A1 | 11/2004 | Ruane | |
| 2005/0149035 A1 * | 7/2005 | Pimenta et al. | 606/86 |
| 2007/0073111 A1 | 3/2007 | Bass | |
| 2007/0100212 A1 * | 5/2007 | Pimenta et al. | 600/210 |
| 2007/0156024 A1 | 7/2007 | Frasier et al. | |
| 2007/0238932 A1 | 10/2007 | Jones et al. | |
| 2007/0282171 A1 | 12/2007 | Karpowicz et al. | |
| 2008/0058606 A1 * | 3/2008 | Miles et al. | 600/214 |
| 2008/0215081 A1 | 9/2008 | Hsueh et al. | |
| 2008/0262318 A1 | 10/2008 | Gorek et al. | |
| 2008/0319290 A1 | 12/2008 | Mao et al. | |
| 2009/0069634 A1 | 3/2009 | Larkin | |
| 2009/0124860 A1 * | 5/2009 | Miles et al. | 600/202 |
| 2009/0227845 A1 | 9/2009 | Lo et al. | |
| 2009/0259107 A1 | 10/2009 | Crenshaw et al. | |
| 2010/0022845 A1 | 1/2010 | Ott et al. | |
| 2010/0076502 A1 * | 3/2010 | Guyer et al. | 606/86 R |
| 2010/0222644 A1 | 9/2010 | Sebastian et al. | |
| 2010/0317989 A1 | 12/2010 | Gharib et al. | |
| 2011/0034779 A1 * | 2/2011 | Louftus et al. | 600/210 |
| 2011/0144439 A1 | 6/2011 | Miles et al. | |
| 2011/0257487 A1 * | 10/2011 | Thalgott et al. | 600/208 |
| 2012/0010471 A1 * | 1/2012 | Mire et al. | 600/210 |
| 2012/0046527 A1 * | 2/2012 | Cianfrani et al. | 600/232 |
| 2012/0245431 A1 * | 9/2012 | Baudouin et al. | 600/213 |
| 2013/0103103 A1 * | 4/2013 | Mire et al. | 606/86 A |
| 2013/0261401 A1 * | 10/2013 | Hawkins et al. | 600/213 |
| 2013/0274557 A1 * | 10/2013 | Bowman et al. | 600/202 |
| 2014/0039264 A1 * | 2/2014 | Heiman | 600/202 |
| 2014/0088367 A1 * | 3/2014 | DiMauro et al. | 600/202 |
| 2014/0135584 A1 * | 5/2014 | Lee et al. | 600/202 |
| 2014/0172002 A1 * | 6/2014 | Predick | 606/191 |
| 2014/0257035 A1 * | 9/2014 | Blain | 600/104 |
| 2014/0275800 A1 * | 9/2014 | Miles et al. | 600/210 |
| 2015/0051448 A1 * | 2/2015 | Hunt et al. | 600/214 |

FOREIGN PATENT DOCUMENTS

| | | |
|---|---|---|
| JP | 2003-169809 | 6/2003 |
| WO | WO 2004/091426 | 10/2004 |
| WO | WO 2005/094695 | 10/2005 |
| WO | WO 2005/096735 | 10/2005 |
| WO | WO 2007/016368 | 2/2007 |
| WO | WO 2007/087536 | 2/2007 |
| WO | WO 2011/069036 | 6/2011 |
| WO | WO 2011/112878 | 9/2011 |

OTHER PUBLICATIONS

European Patent Application No. 13163266.3: European Search Report dated Oct. 30, 2013, 13 pages.

Maxcess, "XLIF Surgical Technique", Nuvasive Creative Spine Technology, wvvw.nuvasive.corn, ©2007, 30 pages.

* cited by examiner

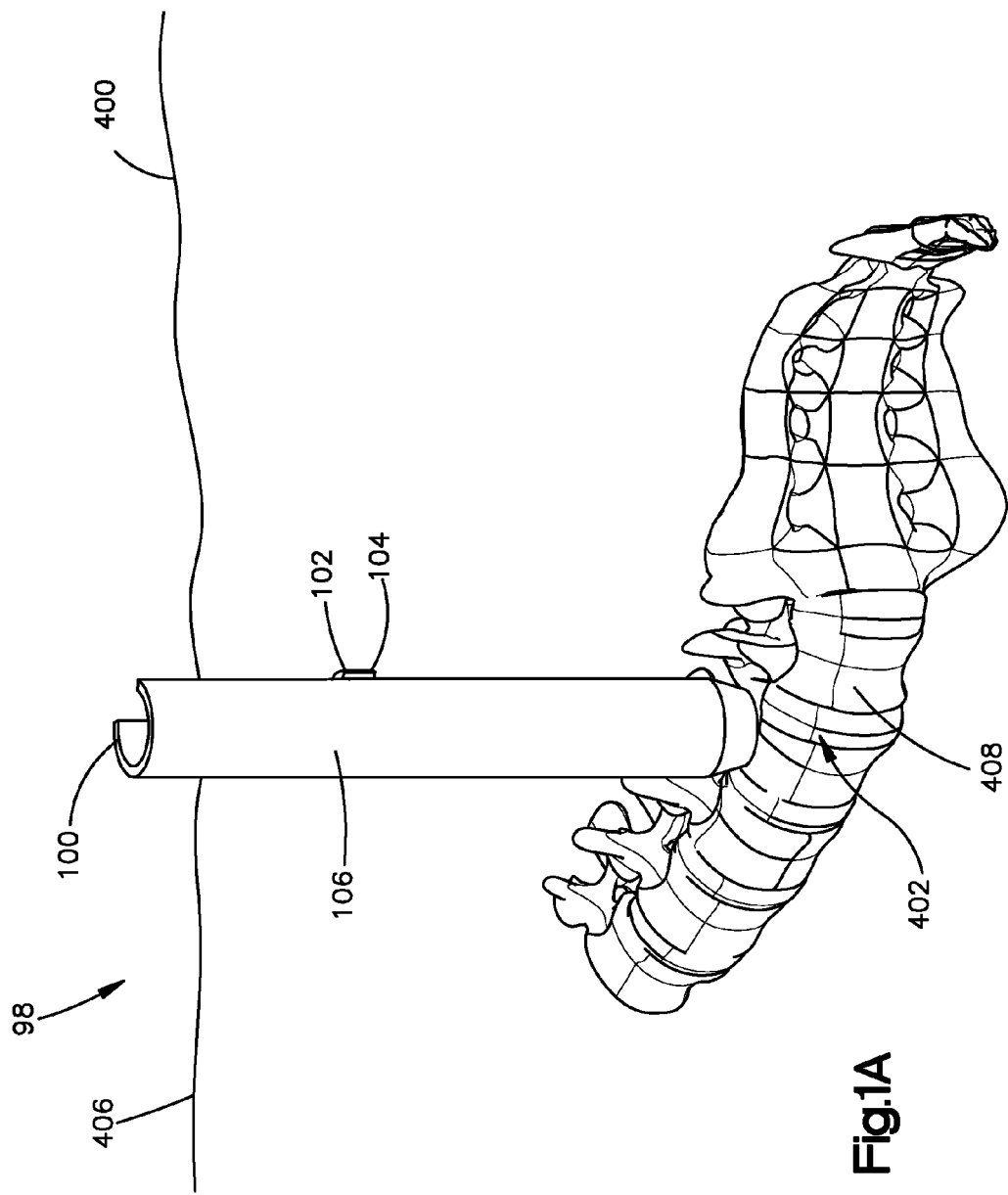

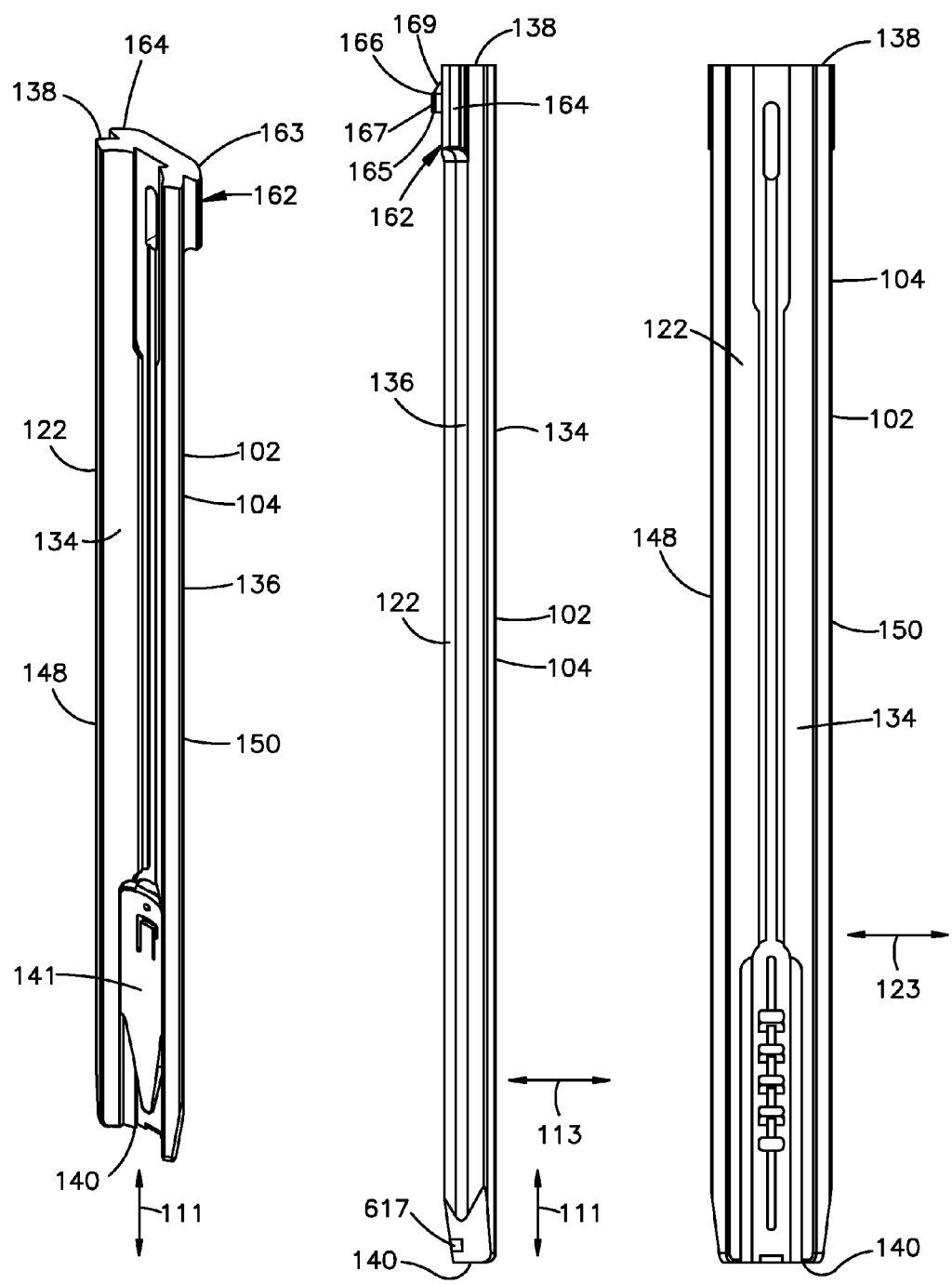

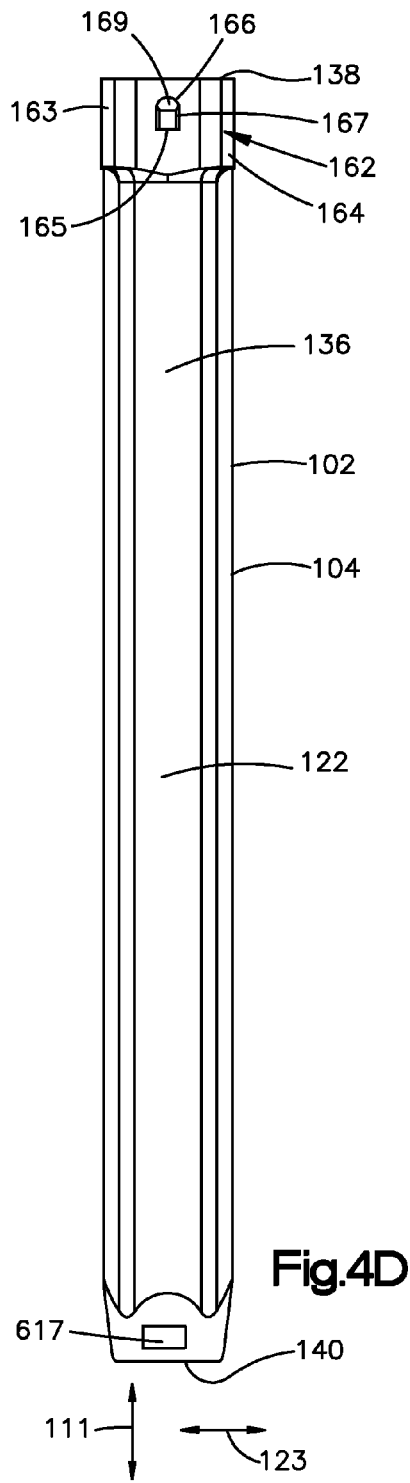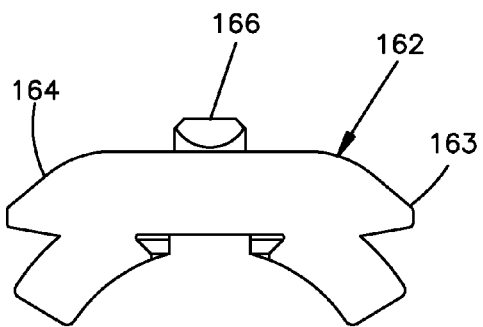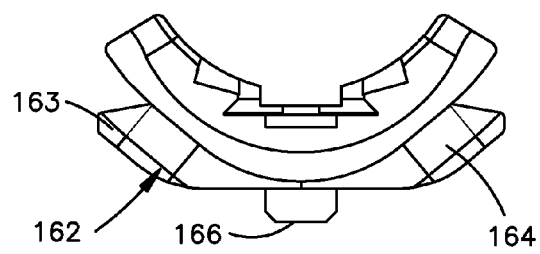
Fig.4D
Fig.4E
Fig.4F

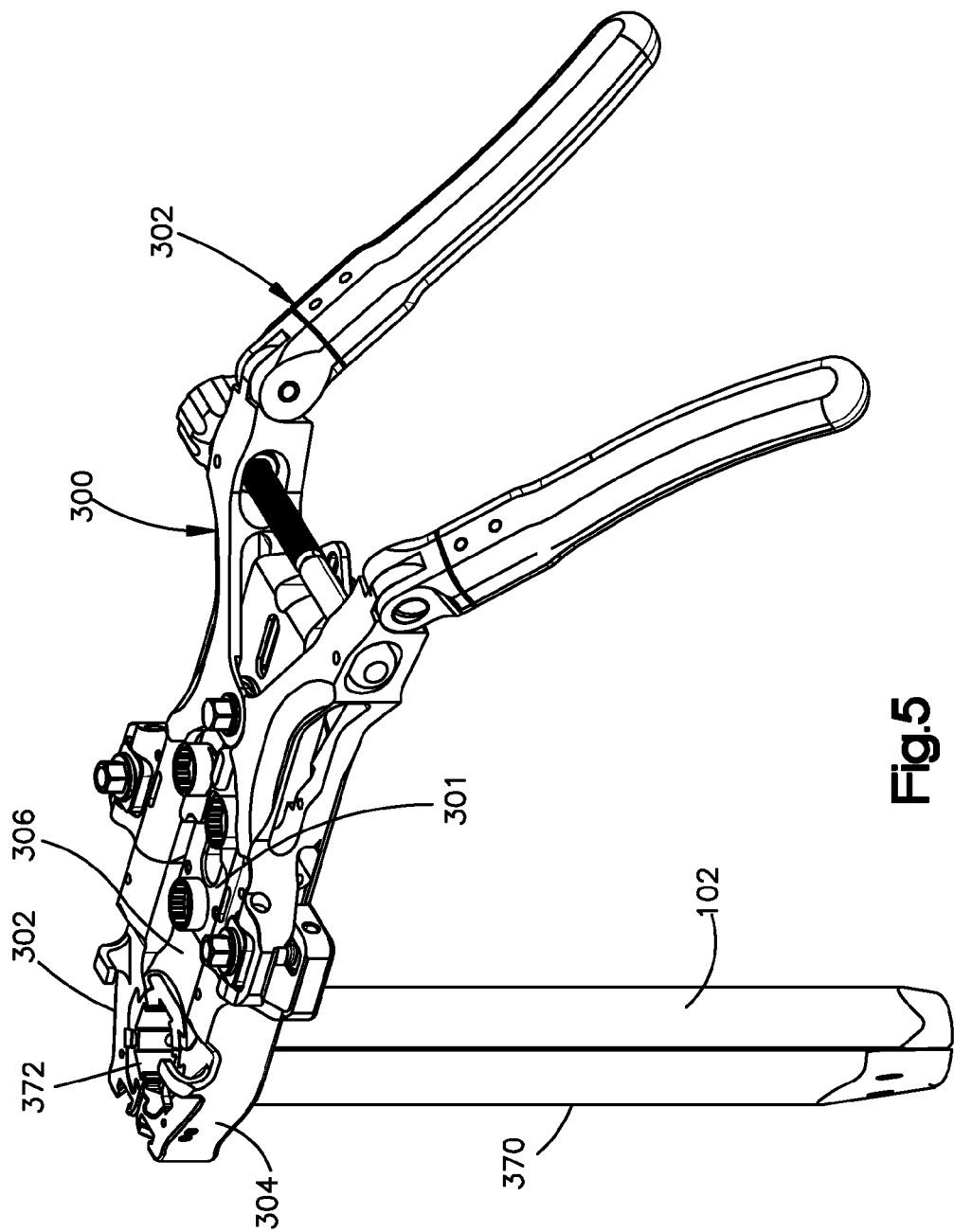

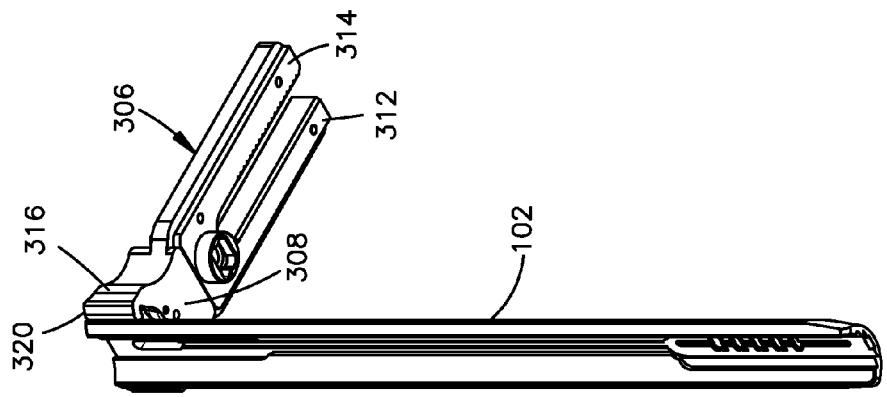
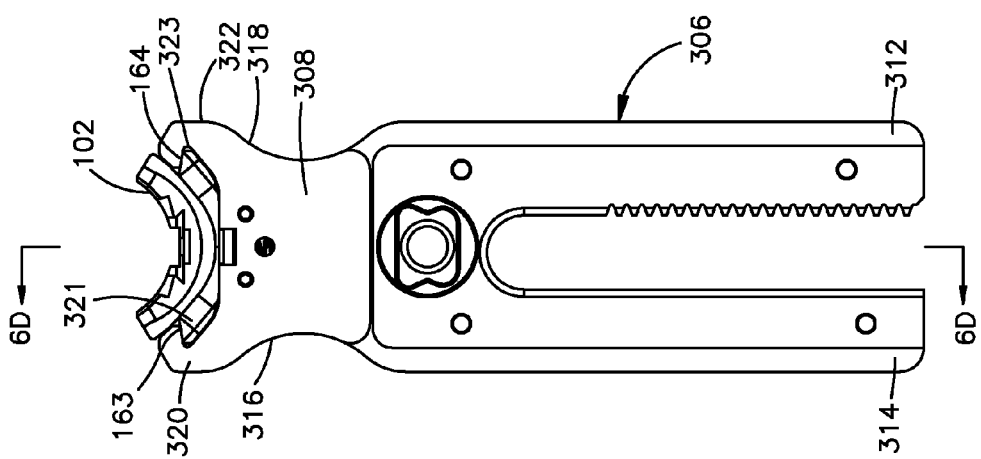
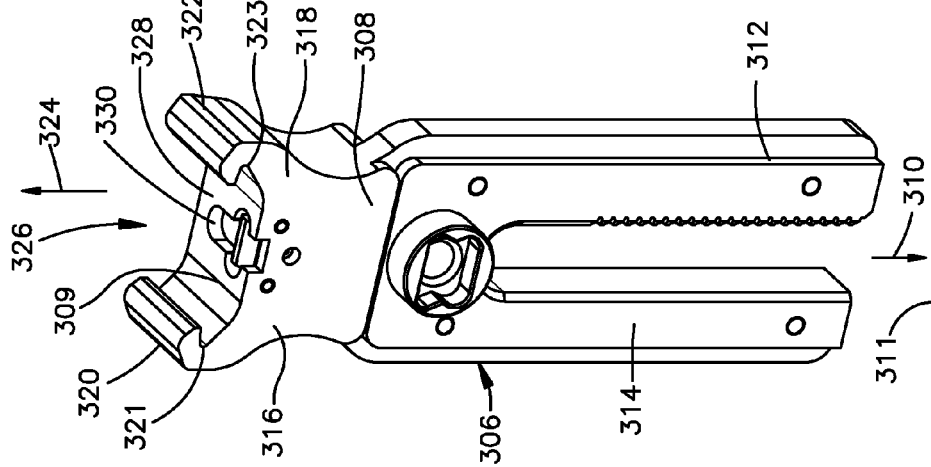

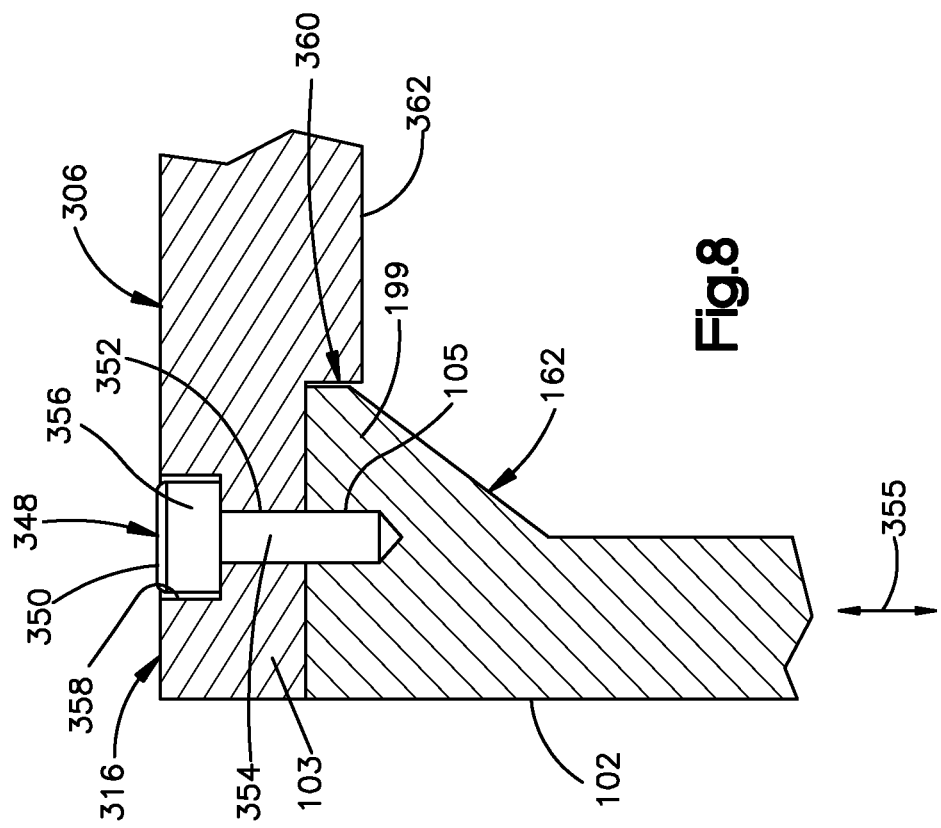
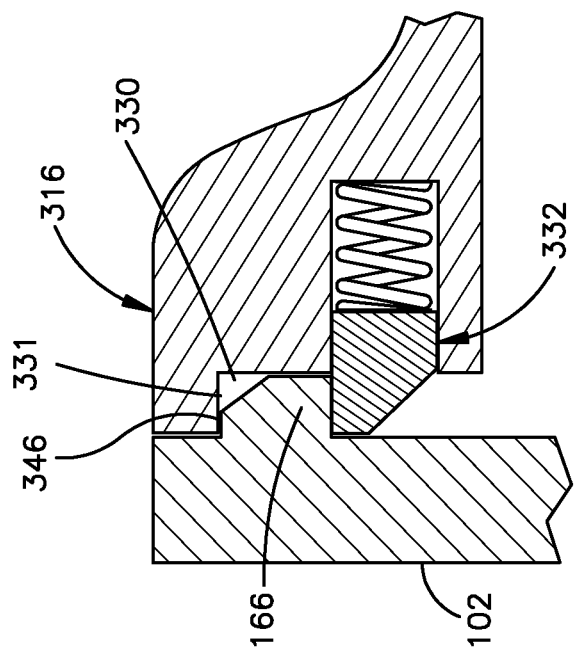

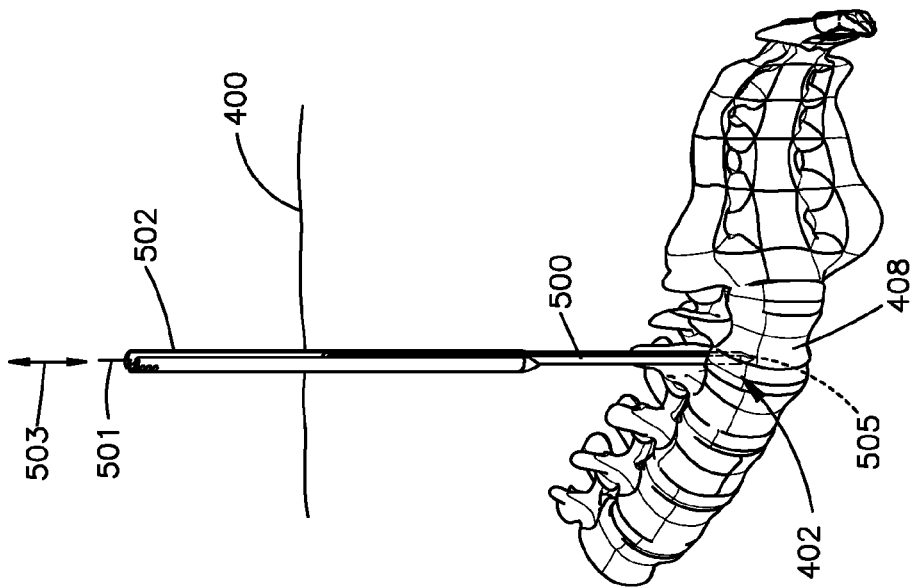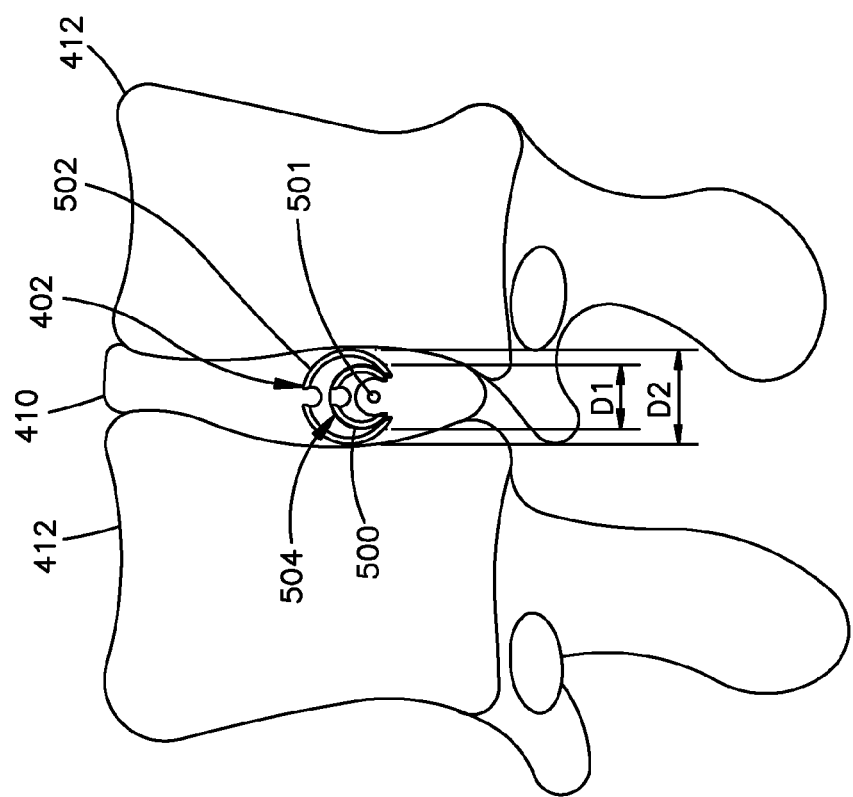

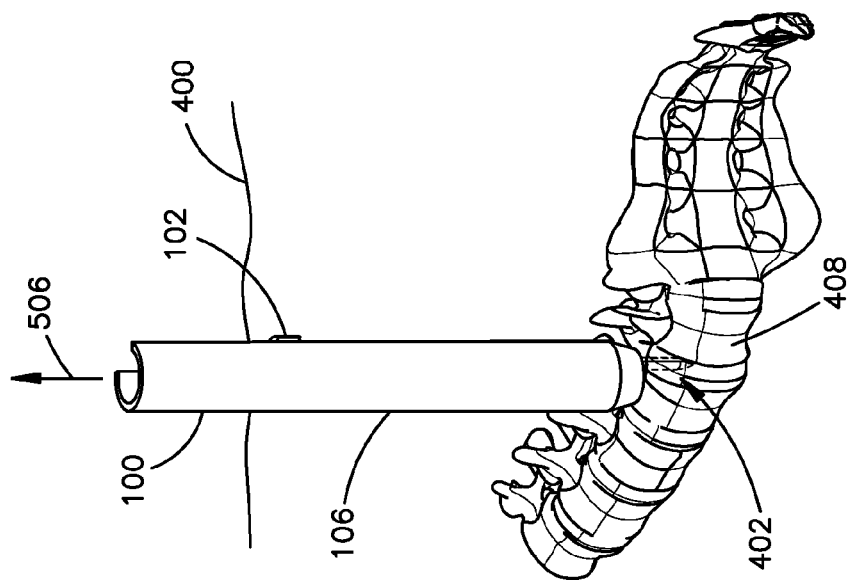
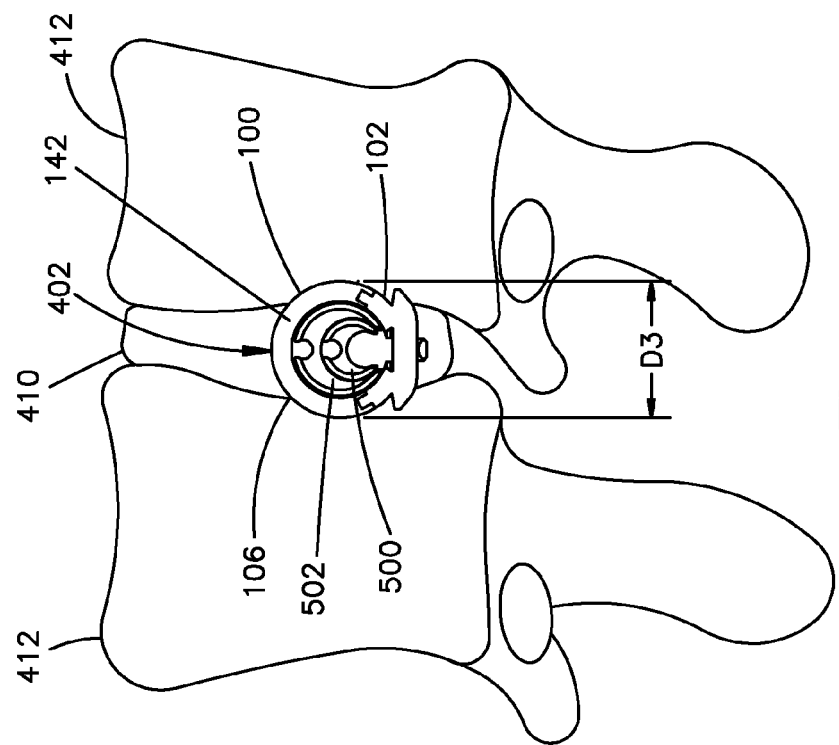
Fig.10A
Fig.10B

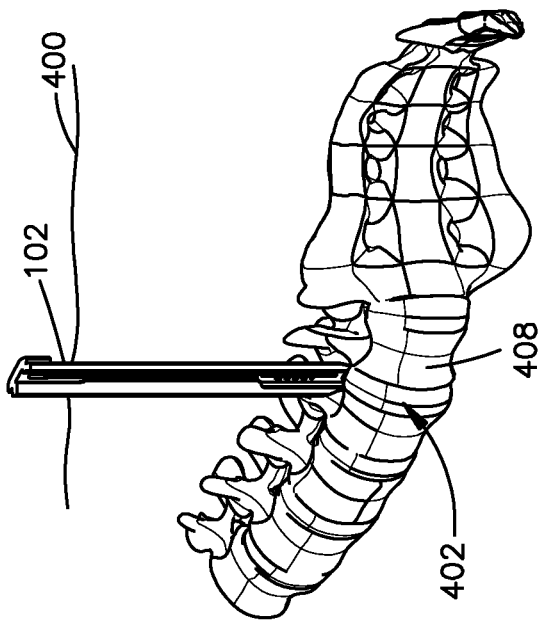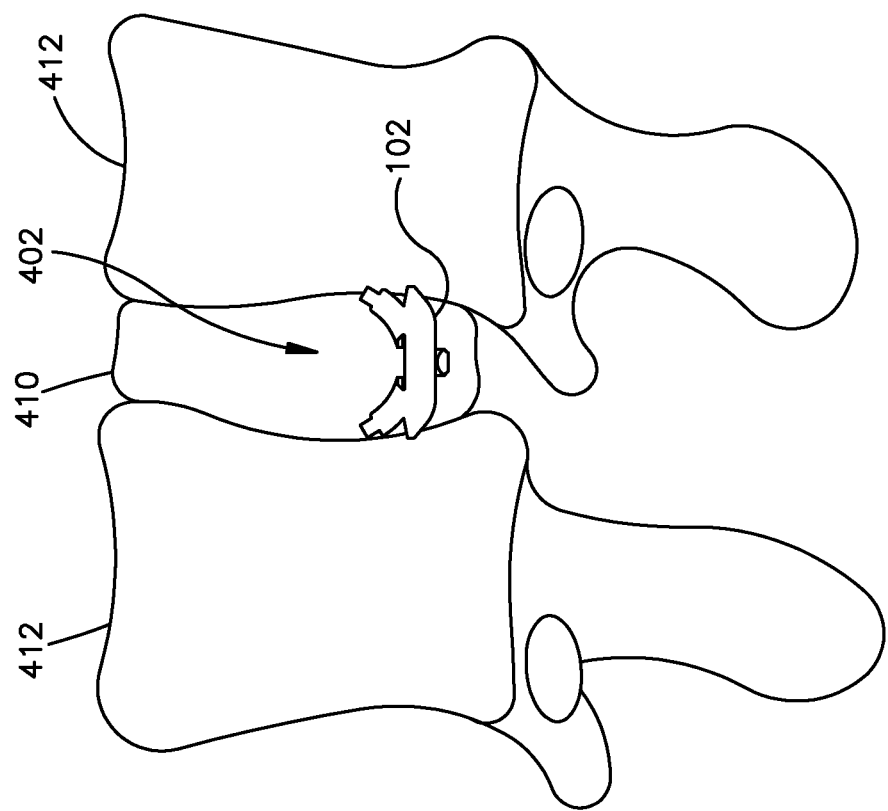

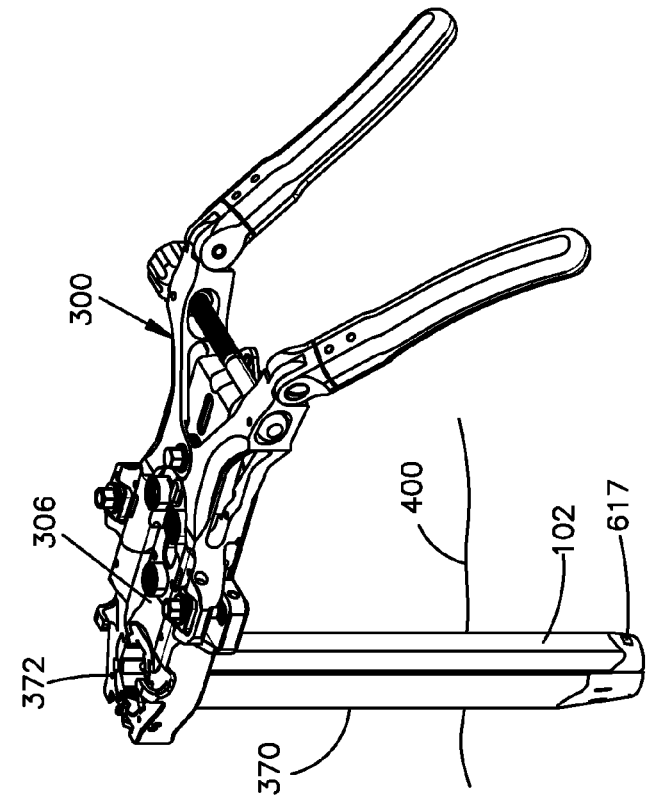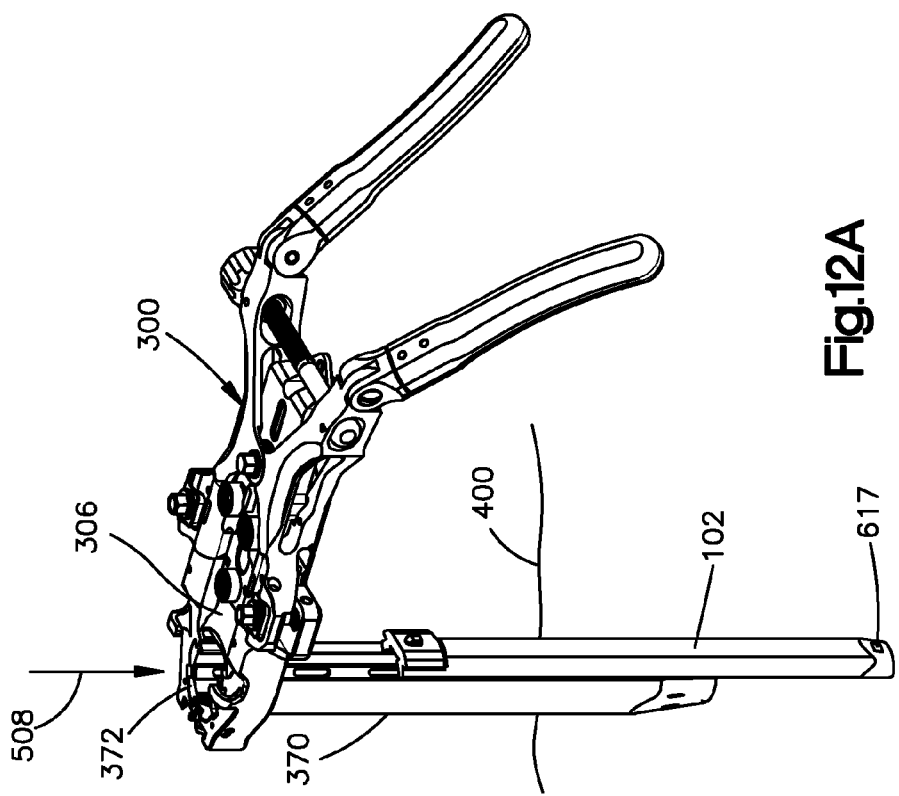

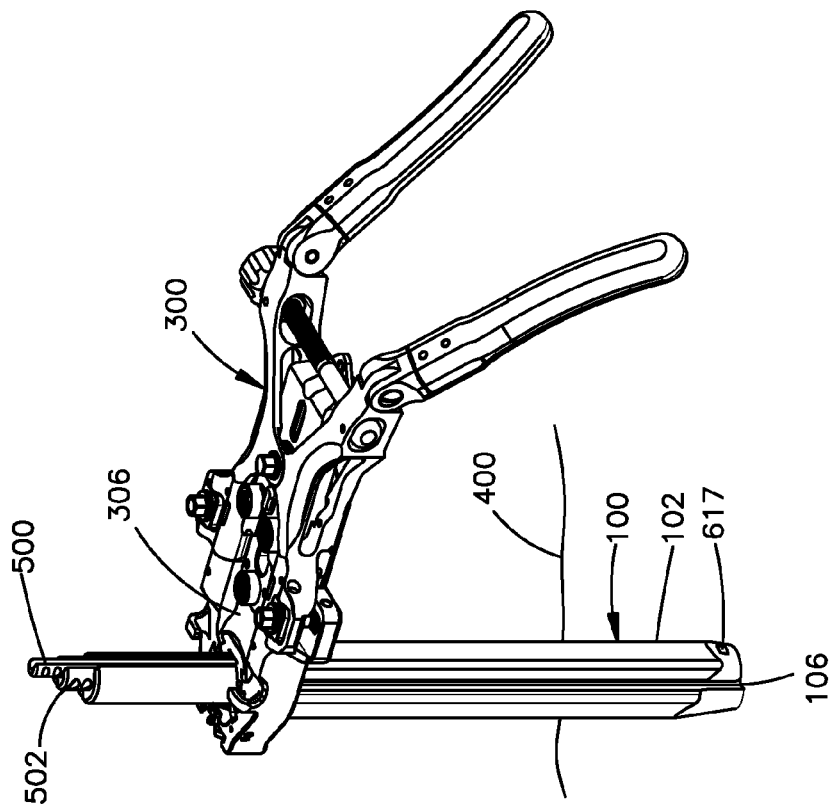
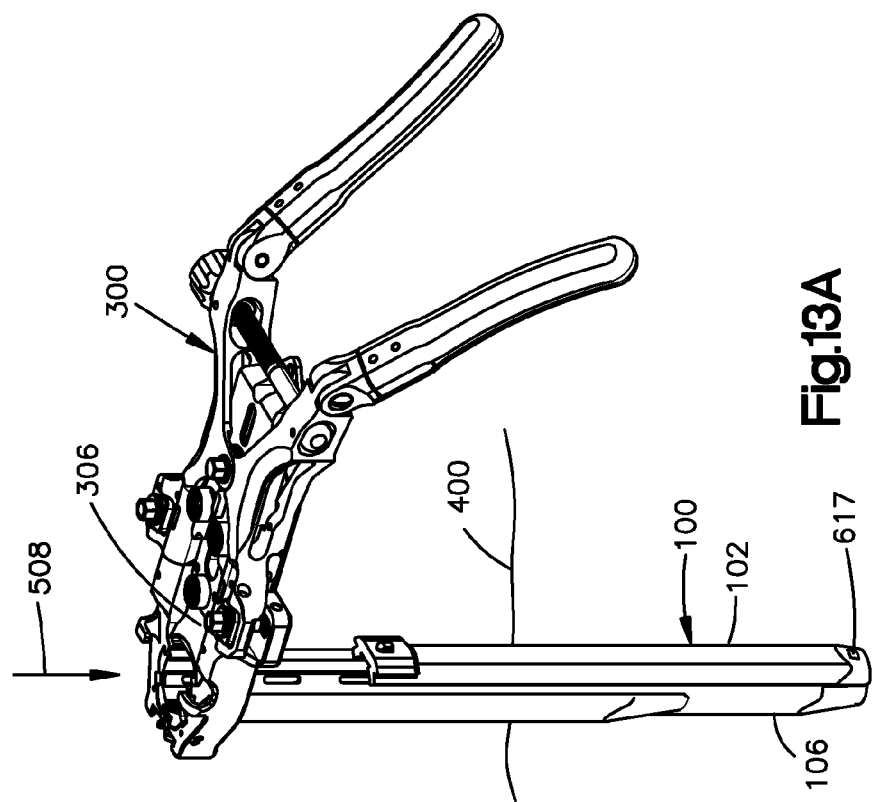
Fig.13A
Fig.13B

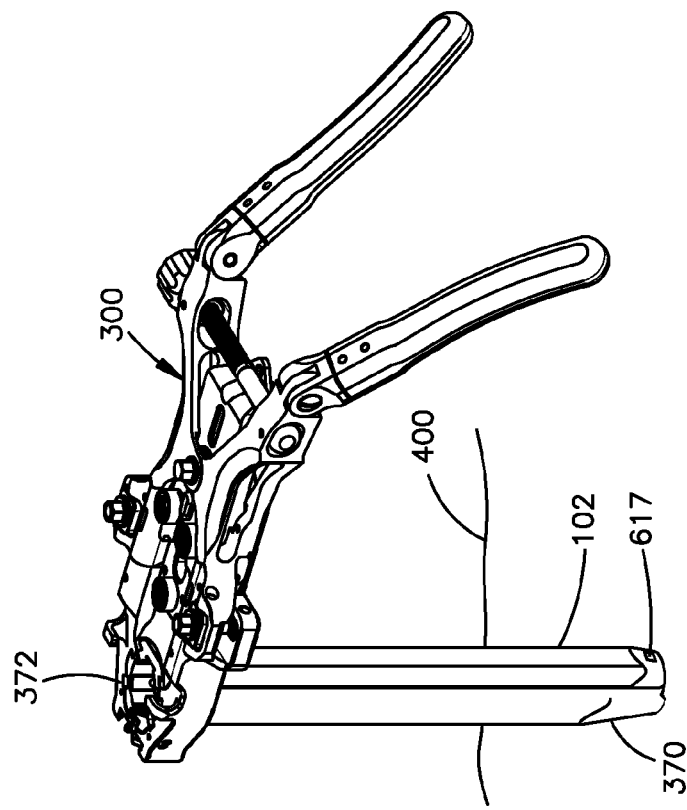
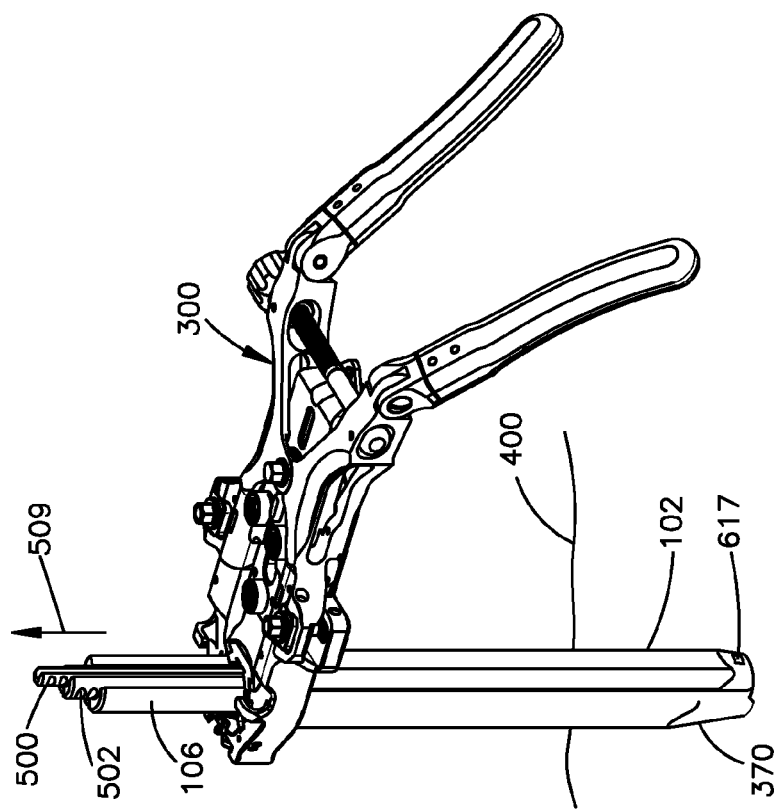

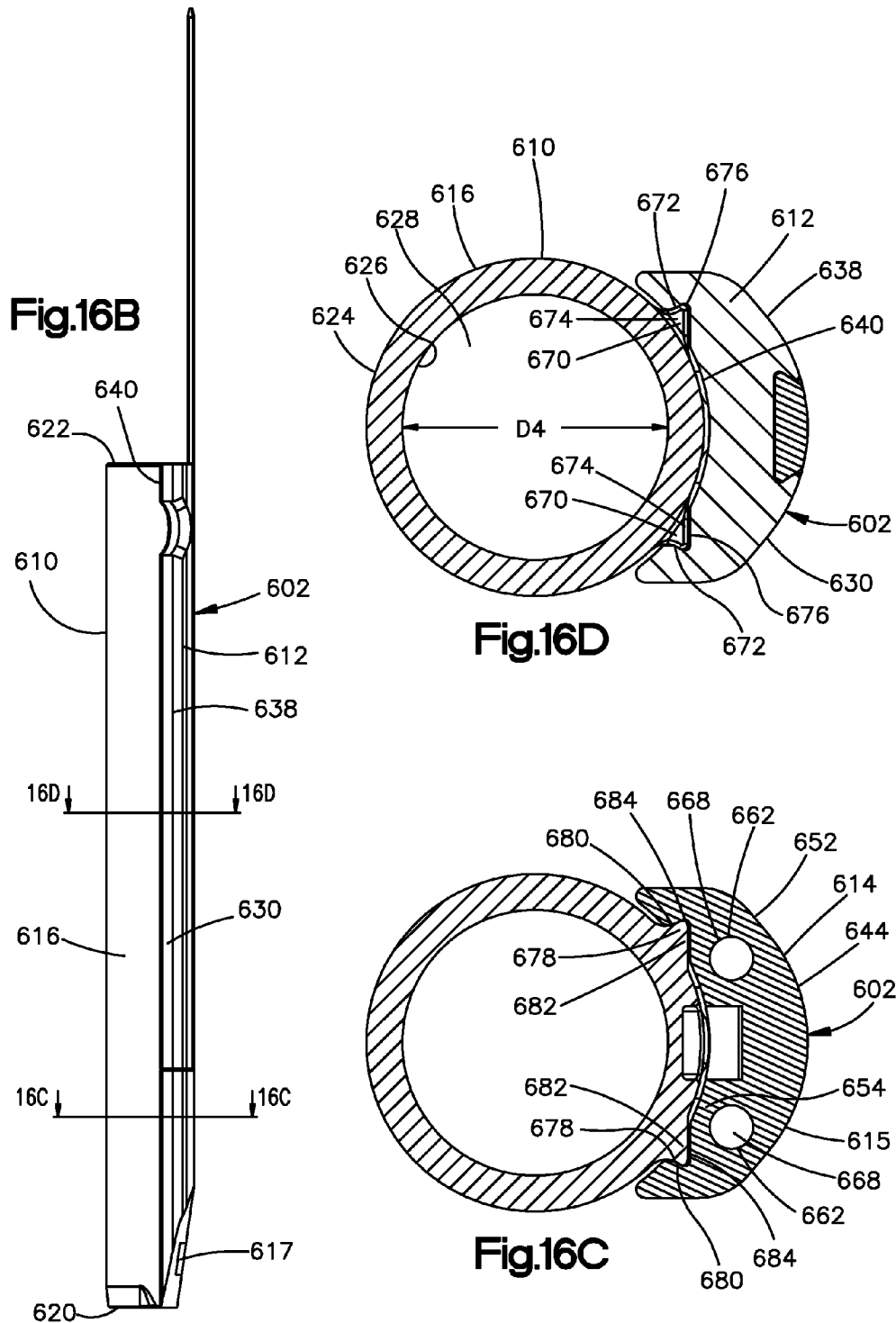

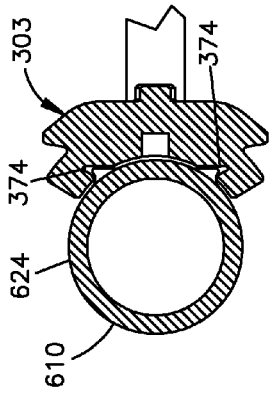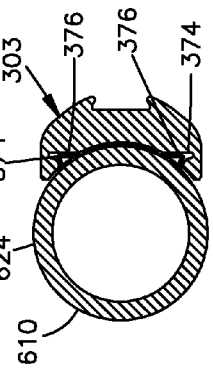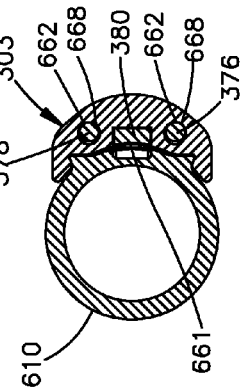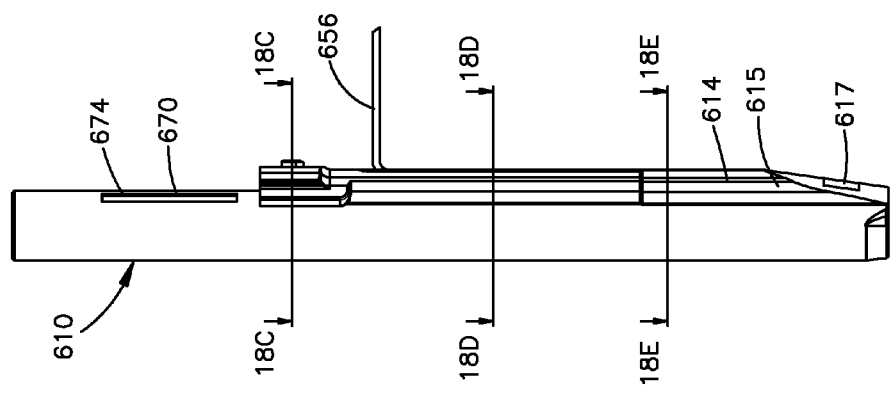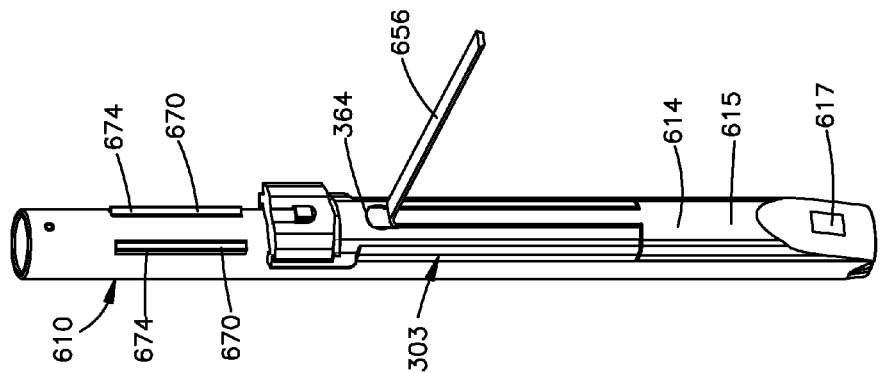

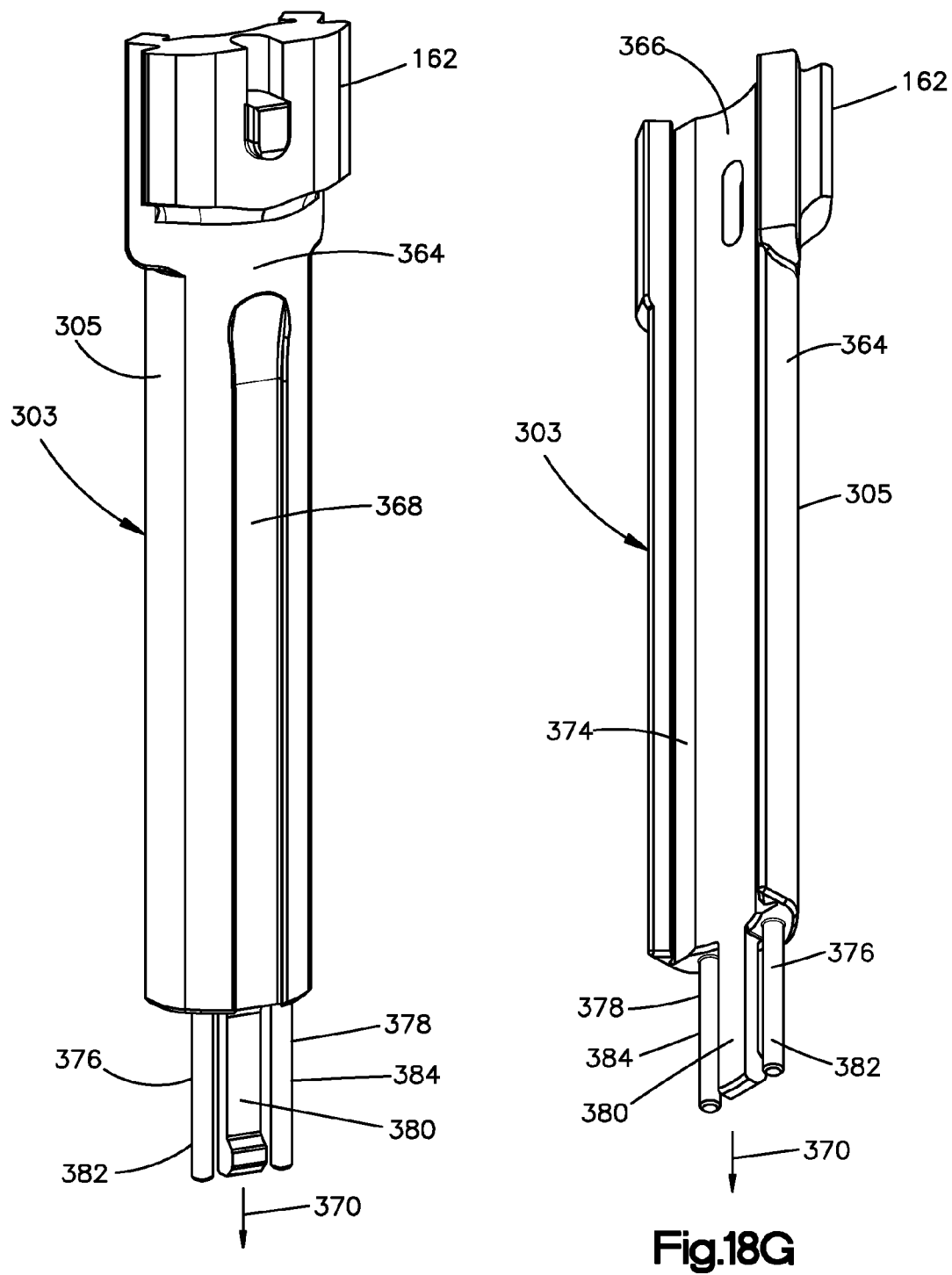

DETACHABLE DILATOR BLADE

FIELD OF DISCLOSURE

The present disclosure generally relates to apparatus, systems, and methods for performing minimally invasive surgery, and more particularly, to dilator assemblies, retractors, systems, and methods for accessing a surgical site to conduct a surgical procedure.

BACKGROUND

In some surgical procedures, surgeons employ open surgery or minimally invasive techniques to access a target site within the patient's body. Open surgery techniques typically require large incisions and high amounts of tissue displacement to gain access to the surgical target site. Due to the large incisions and high amounts of tissue displacement, patients who undergo open surgery usually require a relatively long recovery time. Minimally invasive techniques, in contrast, involve significantly smaller incisions and require less tissue displacement. As a consequence, patients who undergo minimally invasive procedure have significantly shorter recovery time than patients who undergo open surgery.

In view of the advantages of minimally invasive procedures over open surgery, surgical access systems have been developed to access a surgical target site using a minimally invasive approach. For example, surgical dilators, retractors, and systems typically displace or retract tissue to establish an operative corridor to a surgical target site. Surgeons have employed known surgical access retractors and systems in different kinds of surgeries. In spinal surgeries, for example, spinal access systems can be used to retract tissue in order to perform posterior lumbar interbody fusion (PLIF), anterior lumber interbody fusion (ALIF), or any other suitable spinal approach and surgery. A surgical target site can also be accessed via antero-lateral access, postero-lateral access, and direct-lateral access.

SUMMARY

The present disclosure relates to tissue retraction systems configured to dilate a tissue body. In one embodiment, the tissue retraction system generally includes a dilator and a first retractor member. The dilator is configured to be inserted into the tissue body toward a surgical site, and includes a dilator body that is elongate along a longitudinal direction and sized to dilate the tissue body. Furthermore, the dilator includes at least one engagement member. The first retractor member includes a body and at least one engagement member that is configured to attach to the at least one engagement member of the dilator so as to removably attach the retractor member to the dilator body. The first retractor member and the dilator cooperate so as to define a passageway when the first retractor member is attached to the dilator body. The tissue retraction system further includes a retractor assembly. The retraction assembly includes a retractor body and at least a second retractor member that is movably supported by the retractor body. The retractor body is configured to be attached to the first retractor member.

The present disclosure also relates to methods of accessing a surgical site. In an embodiment, the method includes the following steps: inserting a dilator assembly into a tissue body, the dilator assembly comprising a dilator and a retractor member removably attached to the dilator; advancing the dilator assembly toward the surgical site to dilate at least a portion of the tissue body; removing the dilator from the tissue body while leaving the retractor member in the tissue body; and attaching a retractor assembly to the retractor member disposed in the tissue body.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 1A is a perspective view of a dilator assembly constructed in accordance with an embodiment of the present disclosure, including a dilator and a retractor member removably attached to the dilator, showing the dilator assembly disposed adjacent to a spinal column;

FIG. 4A is a perspective view of the retractor member shown in FIG. 1;

FIG. 4B is a side elevation view of the retractor member shown in FIG. 4A;

FIG. 4C is a front elevation view of the retractor member shown in FIG. 4A;

FIG. 4D is a rear elevation view of the retractor member shown in FIG. 4A;

FIG. 4E is a top plan view of the retractor member shown in FIG. 4A;

FIG. 4F is a bottom plan view of the retractor member shown in FIG. 4A;

FIG. 5 is a perspective view of the retractor assembly shown in FIG. 2A;

FIG. 6A is a perspective view of a portion of the retractor body shown in FIG. 5;

FIG. 6B is a top plan view of the portion of the retractor body shown in FIG. 6A, attached to the retractor member shown in FIG. 1;

FIG. 6C is a perspective view of the portion of the retractor body and the retractor member shown in FIG. 6B;

FIG. 7 is a cross-sectional side view of the portion of the retractor body and the retractor member similar to FIG. 6B, but showing the retractor member connected to the retractor body in accordance with an alternative embodiment;

FIG. 8 is a cross-sectional side view of the portion of the retractor body and the retractor member similar to FIG. 6B, but showing the retractor member connected to the retractor body in accordance with an alternative embodiment;

FIG. 9A is a top view of a first dilator and an obturator disposed in the surgical site;

FIG. 9B is a perspective view of a perspective view of the first dilator and the obturator disposed in the surgical site;

FIG. 10A is a top view of the dilator assembly shown in FIG. 1A disposed over the first dilator and the obturator;

FIG. 10B is a perspective view of the dilator assembly shown in FIG. 1A disposed over the first dilator and the obturator;

FIG. 11A is a top view of the retractor member shown in FIG. 4A disposed adjacent the surgical site;

FIG. 11B is a perspective view of the retractor member shown in FIG. 4A disposed adjacent the surgical site;

FIG. 12A is a perspective view the retractor assembly shown in FIG. 2A being advanced toward the retractor member shown in FIG. 4A;

FIG. 12B is a perspective view of the retractor member shown in FIG. 4A attached to the retractor assembly shown in FIG. 2A;

FIG. 13A is a perspective view of the retractor assembly shown in FIG. 2A being advanced along the dilator assembly shown in FIG. 1A;

FIG. 13B is a perspective view of the refractor assembly shown in FIG. 2A being connected to the retractor member shown in FIG. 4A;

FIG. 14A is a perspective view of the retractor assembly shown in FIG. 2A partially disposed in the tissue body, and the dilators being removed from the tissue body;

FIG. 14B is a perspective view of the refractor assembly shown in FIG. 2A after the dilators have been removed from the tissue body;

FIG. 16B is a side elevation view of the dilator assembly shown in FIG. 16A connected to each other;

FIG. 16C is a top cross-sectional view of the dilator assembly shown in FIG. 16A, taken across section line 16C-16C;

FIG. 16D is a top cross-sectional view of the dilator assembly shown in FIG. 16A, taken across section line 16D-16D;

FIG. 18A is a perspective view of a partial retractor member coupled to the dilator and a neuromonitoring member;

FIG. 18B is a side elevation view of the partial retractor member coupled to the dilator and the neuromonitoring member;

FIG. 18C is a cross-sectional view of the partial retractor member coupled to the dilator and the neuromonitoring member, taken along section line 18C-18C of FIG. 18B;

FIG. 18D is a cross-sectional view of the partial retractor member coupled to the dilator and the neuromonitoring member, taken along section line 18D-18D of FIG. 18B;

FIG. 18E is a cross-sectional view of the partial retractor member coupled to the dilator and the neuromonitoring member, taken along section line 18E-18E of FIG. 18B;

FIG. 18F is a rear perspective view of the partial retractor member shown in FIG. 18A; and FIG. 18G is front perspective view of the partial retractor member shown in FIG. 18A

DETAILED DESCRIPTION OF THE DRAWINGS

Figure 1B:
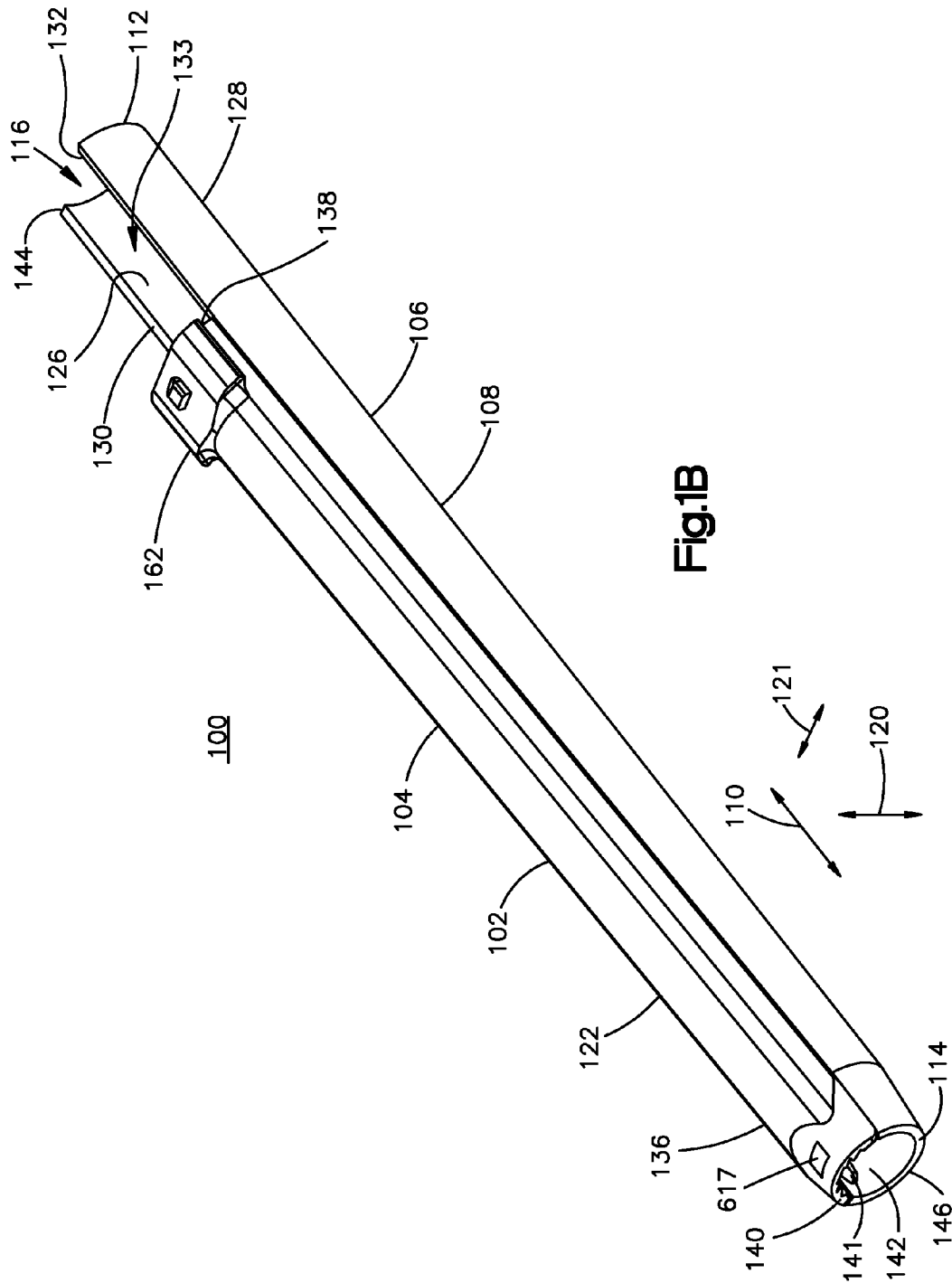
FIG. 1B is a perspective view of the dilator assembly shown in FIG. 1.

With reference to FIG. 1A-2B, a tissue retraction system 98 can include a dilator 106, a retractor body 301, and a retractor member 102 that is configured to be removably attached to the dilator 106 so as to define a dilator assembly 100 that is configured to be inserted into a tissue body 400 so as to at least partially define a passageway toward a desired surgical site 402. The retractor member 102 and the dilator 106 can cooperate so as to define a passageway toward the surgical site 402. The retractor member 102 can be removed from the dilator 106 and attached to the retractor body 301 so as to define a retractor assembly 300 that is configured to be inserted into the tissue body 400, for instance after the tissue body 400 has been dilated by the dilator assembly 100. The retractor assembly 300 can be actuated from a first contracted position to a second expanded position so as to further dilate the tissue body 400. Thus, it should be appreciated that the tissue retraction system 98 can be configured to dilate the tissue body, for instance from an initial position, to a first dilated position, and further to a second dilated position. The dilator 106 can dilate the tissue body 400 to the first dilated position, and expansion of the retractor assembly 300 can further dilate the tissue body 400 from the first dilated position to the second dilated position. The dilator 106 is also referred to as the first dilator. The retractor member 102 is configured to be attached to a retractor assembly 300 of the type having a refractor body 301 and at least one other retractor member that is movably supported by the retractor body 301, such that the retractor member 102 is spaced from the other retractor member. As described in more detail below, the first dilated position can be a sequentially dilated position. Examples of retractor assemblies are described and illustrated in U.S. Pat. Ser. No. 13/237,710, filed on Sep. 20, 2011, the entire disclosure of which is incorporated by referenced herein.

The tissue body 400 at least partially includes tissue, such as anatomical tissue and a tissue substitute, and can further include an implant or the like. Anatomical tissue can include, but is not limited to, soft tissue such as skin, tendons, ligaments, fascia, fibrous tissues, fat, muscle, nerves, blood vessels, and the like. For example, the tissue body 400 can include a psoas muscle 406, and the surgical site 402 can include a region of the spine 408, such as the lumbar region. Tissue substitutes can include soft tissue substitute, such as a graft.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior," "superior," "inferior," "medial," "lateral," and related words and/or phrases designate preferred positions and orientations in the human body to which reference is made and are not meant to be limiting. The terminology includes the above-listed words, derivatives thereof and words of similar import.

As illustrated in FIGS. 1A-B, the dilator assembly 100 is configured to dilate the tissue body 400 so as to displace portions of the tissue body 400 away from other portions of the tissue body 400. It should be appreciated that when the retractor member 102 is attached to the dilator 106, the dilator assembly 100 can include the dilator 106 and the retractor member 102. The retractor member 102 can be configured as a refractor blade 104 or any alternative suitably constructed member as desired that is configured to be removably supported by, for instance attached to, the dilator 106. For instance, the refractor member 102 can include, but is not limited to, the retractor blade 104, an arm, a rod, a plate, or any apparatus, device, mechanism, or means capable of retracting tissue, such as the tissue body 400.

At least one or both of the dilator assembly 100 and the retractor assembly 300 can include one or more sensors that can, for instance, the sensors can be carried by the dilator 106 and retractor member 102, respectively. The sensors can be configured as probes, electrodes, or the like, that are configured to detect properties or characteristics of the tissue body 400. In use, the sensors can be used for electromyography (EMG), mechanomyogram (MMG), pressure sensing, and/or vibration sensing. The sensors thereby provide output to a user interface so as to provide guidance information to a user that can be used to guide the dilator 106 and the retractor member 102 without impinging upon nerve tissue.

During operation, the dilator assembly 100 can be inserted into the tissue body 400, such as the psoas muscle 406. The dilator assembly 100 can then be advanced toward the surgical site 402, such as the lumbar spine 408, until at least a portion of the dilator assembly 100 reaches a location adjacent to the surgical site 402. The retractor member 102 can be removed from the dilator 106, and the dilator 106 can be removed from the tissue body 400, leaving the retractor member 102 in the tissue body 400. The retractor body 301 can be attached to the retractor member 102, so as to retract the dilated tissue body 400 as discussed in more detail below. For instance, the retractor body 301 can be attached to the retractor member 102 before or after the dilator 106 has been removed from the tissue body 400. The dilator 106 is configured to be inserted into the tissue body 400 toward a surgical site 402.

With continuing reference to FIGS. 1A-B, the dilator assembly 100 defines a first assembly end 144 and a second assembly end 146 that is spaced from the first assembly end 144 along a longitudinal direction 110. The first assembly end 144 can define a proximal end and the second assembly end 146 can define a distal end that is spaced distally with respect to the first assembly end 144 along a distal direction, such that the second assembly end 146 is configured to be positioned adjacent the surgical site 402. The dilator 106 includes, but is not limited to, a dissector, an obturator, a sheath, a sleeve, a trocar, a cannula, a tube, a partial tube, a surgical port, or any device, apparatus, mechanism, or suitable apparatus capable of dilating tissue, such as the tissue body 400. The dilator 106 and the retractor member 102 can be at least partly made from any suitable substantially rigid material, such as suitable metallic and polymeric materials. Suitable metallic materials include, but are not limited to, stainless steel, titanium, aluminum, and alloys thereof. Suitable polymeric materials include, but are not limited to, thermoplastics, such as polyetheretherketone (PEEK).

The dilator 106 includes a dilator body 108 that is elongate along the longitudinal direction 110 and is sized to dilate the tissue body 400 as the dilator 106 is inserted into the tissue body 400. The dilator body 108 defines a proximal or first dilator end 112 and a distal or second dilator end 114. The first dilator end 112 and the second dilator end 114 of the dilator body 108 are spaced apart from each other along the longitudinal direction 110. The dilator body 108 further defines an inner dilator surface 126, an outer dilator surface 128 opposite to the inner dilator surface 126, a first dilator side 130 that is connected between the inner dilator surface 126 and outer dilator surface 128, and a second dilator side 132 disposed between the inner dilator surface 126 and the outer dilator surface 128. For instance, the first and second dilator sides 130 and 132 can define surfaces that extend between the inner and outer dilator surfaces 126 along a transverse direction 120 that extends substantially perpendicular to the longitudinal direction 110. The first and second dilator sides 130 and 132 can be spaced from each other so as to define a gap 133 that is defined between the first and second dilator sides 130 and 132, and is elongate along the longitudinal direction 110. Thus, the dilator body 108 can terminate at the first and second dilator sides 130 and 132. In accordance with one embodiment, the first and second dilator sides 130 and 132 can be spaced from each other along a lateral direction 121 that extends substantially perpendicular to the longitudinal direction 110 and the transverse direction 120; though it should be appreciated that the first and second dilator sides 130 and 132 can be spaced from each other along any suitable direction as desired.

Figure 3A:
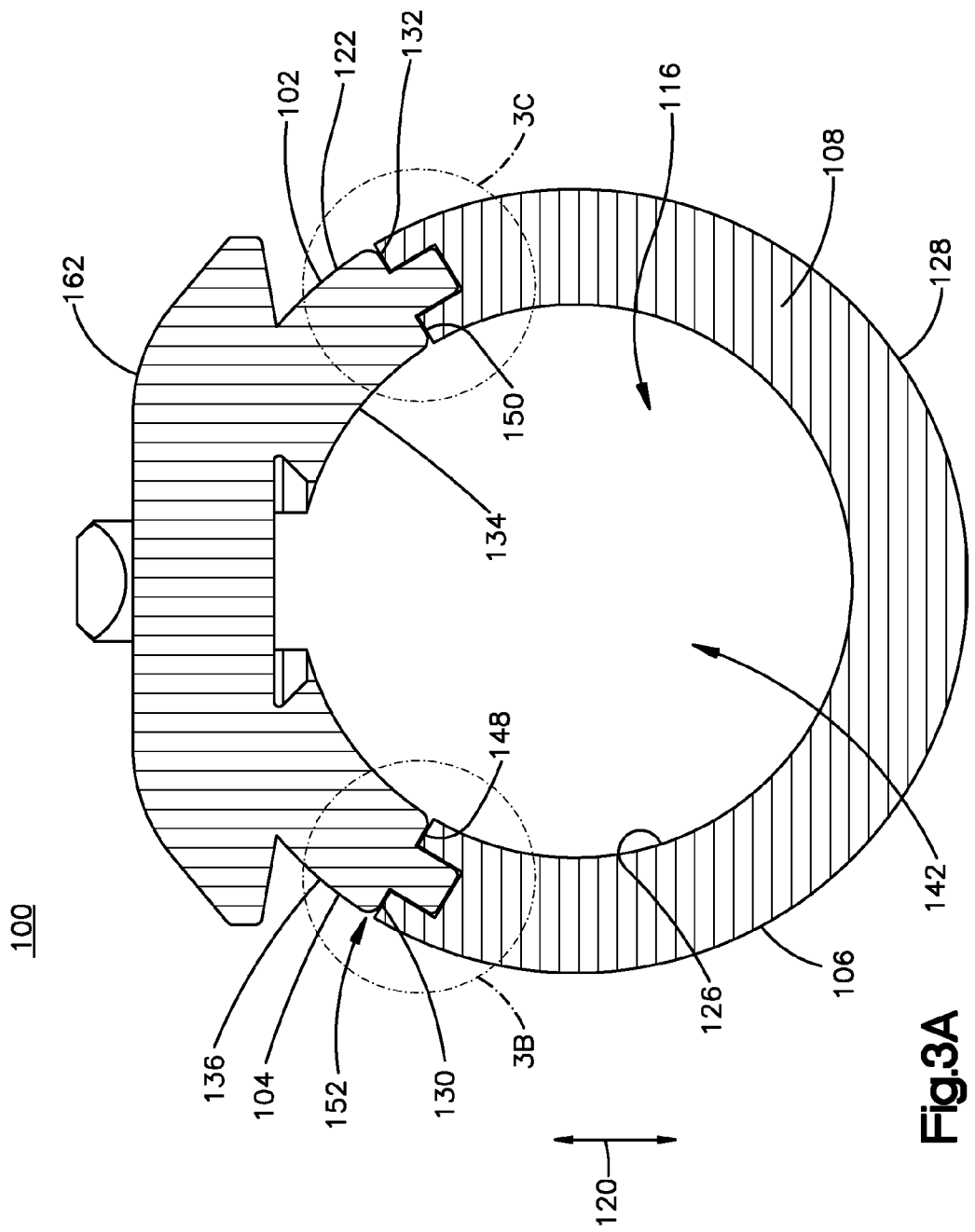
FIG. 3A is a top view of the dilator assembly shown in FIG. 1, showing the retractor member attached to the dilator.
Figure 3C:
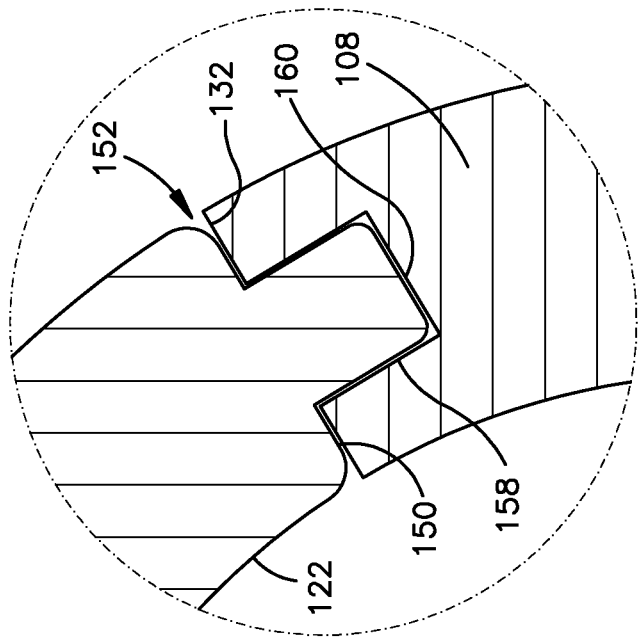
FIG. 3C is an enlarged top view of another portion of the dilator assembly shown in FIG. 3, taken at region 3A.
Figure 3B:
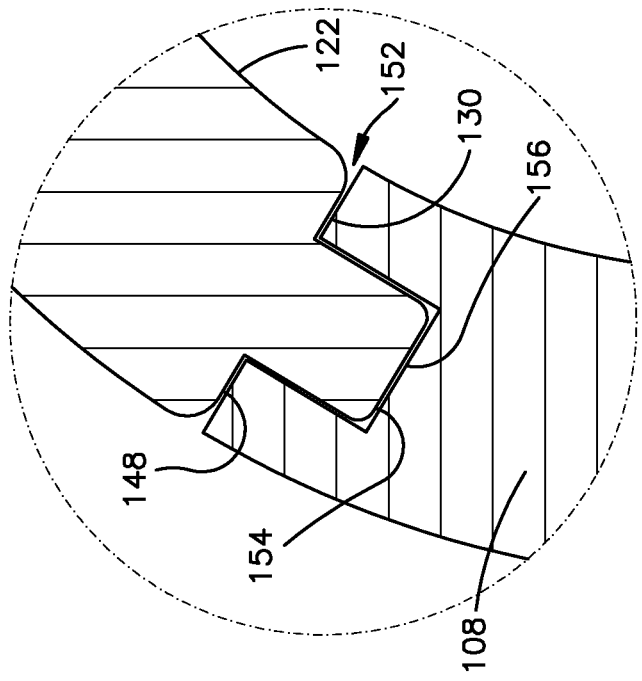
FIG. 3B is an enlarged top view of a first end of the dilator assembly shown in FIG. 3A, taken at region 3B.

The outer dilator surface 128 and the inner dilator surface 126 can have a substantially curved shape or can define any suitable alternative shape. In accordance with the illustrated embodiment, the dilator body 108 can have a substantially partial cylindrical shape. Accordingly, the cross-section of the dilator body 108, taken along a direction that is substantially perpendicular to the longitudinal direction 110, can be substantially arc-shaped or substantially semicircular. It is envisioned, however, that the cross-section of the dilator body 108 can have other suitable shapes. In accordance with the illustrated embodiment, the first and second dilator sides 130 and 132 can be spaced from each other along an angular direction greater than 180 degrees as defined by the dilator body 108. Accordingly, as described in more detail below with reference to FIGS. 3A-C, the retractor member 102 can include a body 122 that defines opposed retractor sides 148 and 150 are spaced from each other along an angular direction less than 180 degrees along the body 122. Thus, the body 122 of the retractor member 102 can terminate at the first and second retractor sides 148 and 150. The cross-sectional shape of the dilator body 108 can be complementary to the cross-sectional shape of the retractor member 102 so that the dilator body 108 and the retractor member 102 cooperate to define a substantially circular cross-section or any alternatively shaped cross-section that is defined along the transverse direction 120. It should be appreciated, however, that the retractor member 102 can be shaped differently from the dilator body 108 in any manner, such that the retractor member 102 is removably attachable to the dilator body 108, for instance so as to at least partially close the gap 133. The body 122 can define a proximal end and a distal end that is spaced from the proximal end along a longitudinal direction. Further, the body 122 can define an inner passageway-facing surface 134 and an opposed outer tissue-facing surface 136. The shim 141 can be movably coupled to the inner-passageway-facing surface 164 of the body 122. The electrode 617 can be attached to the outer tissue-facing surface 136 of the body 122.

The inner dilator surface 126 defines a channel 116 that can extend through the dilator body 108 from the first dilator end 112 to the second dilator end 114 along the longitudinal direction 110. The gap 133 can be in communication with the channel 116 along the transverse direction 120 or any alternative direction that is substantially perpendicular to the longitudinal direction 110. It should be appreciated that the retractor member 102 is attachable to the dilator body 108 so as to close at least a portion of the gap 133. As is described in more detail below, the retractor member 102 can be translatably attached to the dilator body 108 so as translate relative to the dilator body 108, and thus the gap 133, along the longitudinal direction 110. Thus, the gap 133 can be referred to as a variable sized gap. As used herein, the channel 116 can include, but is not limited, to a hole, a slot, a groove, an opening, a cavity, a void, or any open space that is configured and sized to receive another dilator that can define a channel that is smaller than the channel 116, such that the dilator 106 can dilate the tissue body 400 beyond the dilation from the other dilator. Thus, it should be appreciated that the dilator assembly 100 can include one or more dilators that have channels of different sizes that can be fitted over each other so as to sequentially dilate the tissue body 400.

In accordance with the illustrated embodiment, the inner and outer dilator surfaces 126 and 128 extend continuously between the first and second dilator sides 130 and 132. Accordingly, it can be said that the first and second dilator sides 130 and 132 are substantially fixed to each other, such that the channel 116 has a size that is fixed. For instance, the first and second dilator sides 130 and 132 are not configured to move with respect to each other so as to increase the size of the channel 116 when the dilator body 108 is inserted into the tissue body 400. In embodiments where the dilator body 108 is entirely rigid, the first and second dilator sides 130 and 132 are entirely fixed with respect to relative movement. In embodiments where the dilator body 108 is flexible, such that the dilator body 108 can be flexed in response to an applied force, the first and second dilator sides 130 and 132 can be referred to as substantially fixed with respect to each other, and not configured to move with respect to each other once the dilator body 108 is inserted into the tissue body 400. Furthermore, in accordance with the illustrated embodiment, the dilator 106 can include only a single monolithic dilator body 108.

Referring now also to FIGS. 4A-D, the retractor member 102 can be configured as a retractor blade 104, and includes a body 122 that defines a proximal or first end 138 and a distal or second refractor end 140 that is spaced from the first end 138 along a longitudinal direction 111. It should be appreciated that when the retractor member 102 is attached to the dilator 106, the longitudinal direction 111 of the retractor member 102 can be coincident with the longitudinal direction 110 of the dilator 106. The retractor member 102 can further define an inner retractor surface 134 and an opposed outer refractor surface 136 that is spaced from the inner retractor surface 134 along a transverse direction 113 that extends substantially perpendicular to the longitudinal direction 111. It should thus be appreciated that when the retractor member 102 is attached to the dilator 106, the transverse direction 113 of the retractor member 102 can be coincident with the transverse direction 120 of the dilator 106.

The inner and outer retractor surfaces 134 and 136 can extend between the first and second ends 138 and 140, respectively, along the longitudinal direction 111. The retractor member 102 can further define a first retractor side 148 that is connected between the inner retractor surface 134 and outer retractor surface 136, and a second retractor side 150 that is connected between the inner retractor surface 134 and the outer retractor surface 136. For instance, the first and second retractor sides 148 and 150 can define surfaces that extend between the inner and outer refractor surfaces 134 and 136 along a transverse direction 123 that extends substantially perpendicular to the longitudinal direction 111 and the lateral direction 113. In accordance with one embodiment, the first and second retractor sides 148 and 150 can be spaced from each other along a lateral direction 123 that extends substantially perpendicular to the longitudinal direction 110 and the transverse direction 113; though it should be appreciated that the first and second retractor sides 148 and 150 can be spaced from each other along any suitable direction as desired.

At least a portion up to all of the outer retractor surface 136 and the inner retractor surface 134 can have a substantially curved shape along a cross-section that is substantially perpendicular to the longitudinal direction 111, or can be alternatively shaped along the cross-section as desired. The first and second refractor sides 148 and 150 can be spaced a distance substantially equal to a distance that the first and second dilator sides 130 and 132 are spaced (for instance, along the lateral direction 123 and 121, respectively). Accordingly, at least one or both of the first and second retractor sides 148 and 150 are configured to attach to the complementary one or both of the first and second dilator sides 130 and 132, respectively, so as to attach the retractor member 102 to the dilator 106 as illustrated in FIG. 1B.

Referring now to FIGS. 3A-4F, the retractor member 102 can include at least one attachment member, such as a first retractor engagement member 154 and a second retractor engagement member 158 that are carried by the body 122 and are configured to removably attach to the dilator body 108. The retractor member 102 can include an engagement member that is configured to attach to the dilator 106 that is the same as the engagement member that is configured to attach to the refractor assembly 300. The first and second retractor engagement members 154 and 158 can extend out from the body 122, for instance from the first and second sides 148 and 150, respectively. In accordance with the illustrated embodiment, the first and second retractor engagement members 154 and 158 are monolithic with the body 122; though it should be appreciated that the first and second retractor engagement members 154 and 158 can alternatively be separate from the body 122 and attached to the body. In accordance with the illustrated embodiment, the first and second retractor engagement members 154 and 158 are configured as protrusions that extend out from the body 122, for instance from the first and second sides 148 and 150 along a direction that is angularly offset, such as substantially perpendicular, from the first and second sides 148 and 150. The first and second retractor engagement members 154 and 158 can be elongate along the longitudinal direction 111. In accordance with the illustrated embodiment, the first and second engagement members 154 and 158 define a first thickness along a direction that is substantially perpendicular to the longitudinal direction 111, and the body 122 defines a second thickness along the same direction that is substantially perpendicular to the longitudinal direction 111, such that the first thickness is less than the second thickness. For instance, in accordance with one embodiment, the first and second retractor engagement members 154 and 158 can be referred to as tongues that extend out from the first and second sides 148 and 150, respectively. The refractor member 102 can include at least one engagement member that is carried by the body 122 and configured to attach to a dilator 106.

With continuing reference to FIGS. 3A-4F, the dilator 106 can include at least one attachment member, such as a first dilator engagement member 156 and a second dilator engagement member 160 that are carried by the dilator body 108 and are configured to attach to the complementary first and second retractor engagement members 154 and 158, respectively, so as to removably and translatably attach to the retractor member 102 to the dilator body 108. The first and second dilator engagement members 156 and 160 can be configured as recesses that extend into the dilator body 108, for instance into the first and second dilator sides 130 and 132, respectively. The first and second dilator engagement members 156 and 160 can be elongate along the longitudinal direction 110. In accordance with the illustrated embodiment, the first and second dilator engagement members 156 and 160 are monolithic with the dilator body 108; though it should be appreciated that the first and second dilator engagement members 154 and 158 can alternatively be separate from the dilator body 108 and attached to the dilator body 108. In accordance with the illustrated embodiment, the first and second dilator engagement members 156 and 160 are configured as recesses that extend out from the body 122, for instance from the first and second dilator sides 130 and 132 along a direction that is angularly offset, such as substantially perpendicular, from the first and second sides 130 and 132. In accordance with the illustrated embodiment, the first and second dilator engagement members 156 and 160 define a third thickness along a direction that is substantially perpendicular to the longitudinal direction 110, and the dilator body 108 defines a fourth thickness along the same direction that is substantially perpendicular to the longitudinal direction 110, such that the third thickness is less than the fourth thickness. For instance, in accordance with one embodiment, the first and second dilator engagement members 156 and 160 can be referred to as grooves that are recessed into the first and second sides 130 and 132, respectively.

Thus, it should be appreciated that the dilator assembly 100 can include an attachment mechanism 152 that includes the at least one engagement member of the retractor member 102, such as the first and second retractor engagement members 154 and 158, respectively. The attachment mechanism 152 further includes the at least one engagement member of the dilator 106, such as the first and second dilator engagement members 156 and 160. The first retractor engagement member 154 is configured to attach to the first dilator engagement member 156 so as to translatably attach the retractor member 102 to the dilator 106. Similarly, the second retractor engagement member 158 is configured to translatably attach to the second dilator engagement member 160 so as to attach the retractor member 102 to the dilator 106. Thus, the retractor member 102 is configured to translate along the dilator 106, for instance along the longitudinal direction 110.

In accordance with the illustrated embodiment, the first and second retractor engagement members 154 and 158 are configured to be received in the complementary first and second dilator engagement members 156 and 160 so as to translatably attach the refractor member 102 to the dilator 106. Thus, the first and second retractor engagement members 154 and 158 can be referred to as tongues, and the first and second dilator engagement members 156 and 160 can be referred to as grooves, such that the attachment mechanism 152 defines a tongue-and-groove interface that attaches the retractor member 102 to the dilator 106. It should be appreciated, of course, that the first and second retractor engagement members 154 and 158 can be alternatively configured as desired. For instance, the first and second retractor engagement members 154 and 158 can be configured as grooves that are recessed into the body 122, for instance into the sides 148 and 150. Furthermore, it should be appreciated that the first and second dilator engagement members 156 and 160 can be alternatively configured as desired. For instance, the first and second dilator 156 and 160 can be configured as protrusions that extend out from the dilator body 108, for instance from the first and second sides 130 and 132, respectively. The engagement members of the dilator 106 and the retractor member 102 attach such that the retractor member 102 is movable with respect to the dilator 106. In an embodiment, the engagement members of the dilator 106 and the retractor member 102 attach such that the retractor member 102 can translate relative to the dilator 106.

Referring to FIG. 1B and FIGS. 3A-C, the retractor member 102 can be attached to the dilator 106 by aligning the first and second retractor engagement members 154 and 158 with the first and second dilator engagement members 156 and 160 along the longitudinal direction 110. Next, one or both of the retractor member 102 and the dilator 106 can be translated toward the other along the longitudinal direction such that the one of 1) the first and second retractor engagement members 154 and 158 and 2) the first and second dilator engagement members 156 and 160 is received in the other along a first direction, for instance one of 1) the proximal end of the dilator body 108 and the distal end of the body 122, and 2) the distal end of the dilator body 108 and the proximal end of the body 122. Once the first and second retractor engagement members 154 and 158 are attached to the first and second dilator engagement members 156 and 160, the refractor member 102 can translate along the longitudinal direction 110 with respect to the dilator 106. For instance, the retractor member 102 can be positioned such that the distal end of the body 122 can be substantially aligned with the distal end of the dilator body 108, or can be offset proximally or distally with respect to the distal end of the dilator body 108. The retractor member 102 can be subsequently removed from the dilator 106 by translating one of the retractor member 102 and the dilator 106 with respect to the other along a second direction that is opposite the first direction until the retractor member 102 is spaced from the dilator 106 along the longitudinal direction 110, which causes the first and second retractor engagement members 154 and 158 detach from the first and second dilator engagement members 156 and 160. The refractor member 102 can further include a tissue anchor such as shim 141. The shim 141 can be configured to be inserted into a tissue portion in order to anchor the retractor member 102 to that tissue portion. The shim 141 can be movably secured to an inner surface of the retractor member 102. The retractor member 102 further includes one or more electrodes 617 that are configured to detect properties or characteristics of the tissue body. For example, the electrode 617 can monitor the direction, pathology, and proximity of nerves. The electrode 617 can be attached to a surface of the retractor member 102. In the depicted embodiment, the electrode 617 is attached to an outer surface of the retractor member 102. Alternatively, the electrode 617 and associated electrical wiring can be embedded in the retractor member 102. The electrode 617 can be configured to be electrically coupled to an electrical power source.

Furthermore, when the refractor member 102 is attached to the dilator 106, the dilator assembly 100 defines a passageway 142 that is partially defined by the inner retractor surface 134 of the body 122, and is further partially defined by the inner dilator surface 126 of the dilator body 108. It should be appreciated that inner retractor surface 134 can at least partially cover the channel 116 of the dilator 106 so as to define the passageway 142. For instance, the inner retractor surface 134 can enclose the channel 116, such that the passageway 142 is enclosed along all directions that are substantially perpendicular to the longitudinal direction 110. Alternatively, the inner retractor surface 134 can partially enclose the channel 116, such that a portion of the passageway can be open along a direction substantially perpendicular to the longitudinal direction 110. It can thus be said that the body 122, for instance at the inner retractor surface 134, at least partially encloses the channel 116 when the retractor member 102 is attached to the dilator 106.

Referring now to FIGS. 4A-F, the retractor member 102 further includes an engagement assembly 162 that is configured to be attached to a portion of a retractor assembly 300 as discussed in detail below. The retractor member 102 can include at least one engagement assembly 162 that is carried by the body 122 and configured to attach to a retractor assembly 300. The engagement assembly 162 can protrude outward from the body 122 in a direction away from the outer refractor surface 136. In the illustrated embodiment, the engagement assembly 162 can protrude from the body 122 at or near the first end 138. Moreover, the engagement assembly 162 can be substantially dovetail shaped. It is envisioned, however, the engagement assembly 162 can have other suitable shapes as desired. The engagement assembly 162 can include at least one engagement member that is configured to attach to the retractor assembly 300. In the depicted embodiment, the engagement assembly 162 includes a first engagement member 164 and a second engagement member 163 that is spaced from the first engagement member 164 along the lateral direction 123. The first and second engagement members 164 and 163 can be configured as protrusions.

With continuing reference to FIGS. 4A-F, the retractor member 102 can further include a lock 166 that protrudes outward from the engagement assembly 162 in a direction away from the outer retractor surface 136. The lock 166 is configured to be attached a portion of the retractor assembly 300 as discussed in detail below. The lock 166 can be configured to secure the body 122 to the refractor assembly 300. In the illustrated embodiment, the lock 166 can be configured as a protrusion that extends from the engagement assembly 162, and is disposed between the first engagement member 164 and the second engagement member 163. The lock 166 defines a top angled surface 169, a central surface 167, and a bottom surface 165. The central surface 167 is connected between the top angled surface 169 and the bottom surface 165. The top angled surface 169 can be configured as a camming surface and can define a plane that is oriented at an oblique angle with respect to the central surface 167, the bottom surface 165, and the longitudinal direction 111. As discussed in detail below, the orientation of the top angled surface 169 with respect to the longitudinal direction 111 facilitates attachment of the retractor member 102 to the refractor assembly 300. The central surface 167 can defines a plane that is oriented substantially parallel to the longitudinal direction 111. The bottom surface 165 can define a plane that is oriented substantially orthogonal to the longitudinal direction 111. As discuss in detail below, the bottom surface 165 is configured to abut a portion of the retractor assembly so as to lock the retractor member 102 to the retractor assembly 300.

Figure 6D:
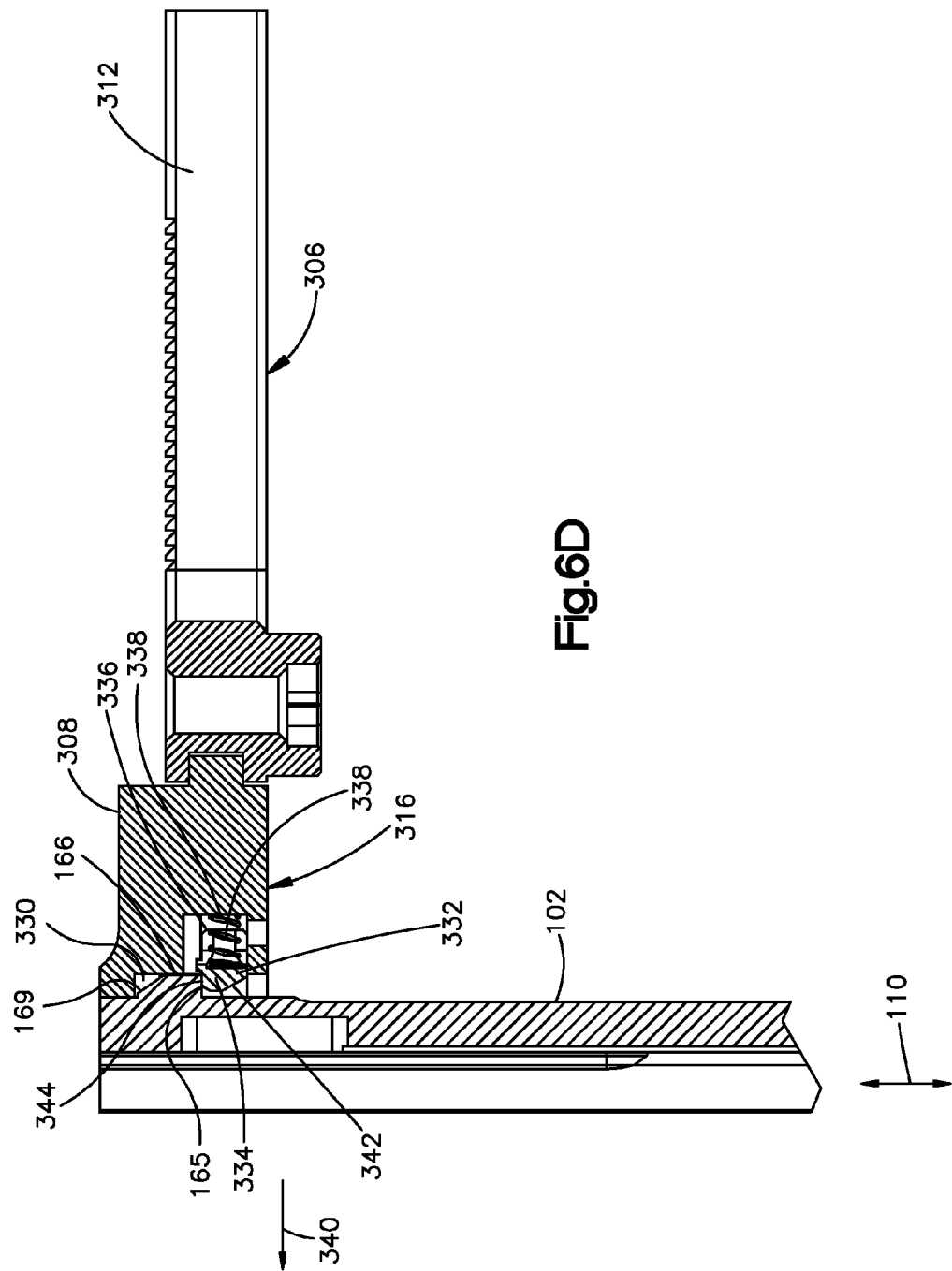
FIG. 6D is a side elevation view of the portion of the retractor body and the retractor member shown in FIG. 6B.

With reference to FIGS. 5-6D, the retractor member 102 can be attached to a retractor assembly 300 via the engagement assembly 162 (FIG. 6). The retractor assembly 300 includes a handle 302, a first side arm 302, a second side arm 304, and a central arm 306 that is disposed between the first side arm 302 and the second side arm 304. The handle 302 can be actuated (e.g., squeezed) to move at least one of the first side arm 302, the second side arm 304, or the central arm 306 relative to each other. Each of the first side arm 302, the second side arm 304, and the central arm 306 is configured to hold a refractor member, such as the retractor member 102. In addition to the retractor member 102, the retractor assembly 300 can hold a cranial retractor member 370 and a caudal retractor member 372. When coupled to the central arm 306, the refractor member 102 can be referred to as a posterior retractor member. Specifically, the first arm 302 is configured to hold the caudal retractor member 372, and the second arm 304 is configured to hold the cranial refractor member 370. Other retractor assemblies can also be used to hold the retractor member 102.

With continuing reference to FIGS. 5-6D, the central arm 306 can be configured to hold the retractor member 102. The central arm 306 includes a central arm body 308, a first leg 312 that protrudes from the central arm body 308, and a second leg 314 that protrudes from the central arm body 308. The first leg 312 and the second leg 314 both protrude from the central arm body 308 in a rearward direction as indicated by arrow 310. Further, the first leg 312 and the second leg 314 are both elongate along the rearward direction indicated by arrow 310, and are configured to be connected to at least a section of the handle 302 or the retractor body 301. The central arm 306 can define an outer arm surface 309 and an engagement member 316, such as clamping device 318, that is configured to hold the retractor member 102. Specifically, the engagement member 316 is configured to attach to the engagement assembly 162 so as to attach the refractor member 102 to a portion of the retractor assembly 300, such as the central arm 306. The engagement member 316 can include at least one engagement member that is configured to be attached to an engagement member of the retractor member 102. For instance, the engagement member 316 can include a first engagement member 321 and a second engagement member 323 that is spaced from the first engagement member 321 along a transverse direction 311. The first engagement member 321 and the second engagement member 323 can be referred as grooves that are recessed into the outer arm surface 309 of the central arm body 308. In particular, the first engagement member 321 is configured to attach to the engagement member 163 of the refractor member, and the second engagement member 323 is configured to attach to the engagement member 164 of the retractor member 102. For instance, the engagement member 163 of the retractor member 102 can be configured as a protrusion, and the engagement member 321 of the central arm 306 can be configured as a groove that is configured to receive the engagement member 163 so as to attach the retractor member 102 to the central arm 306. Similarly, the engagement member 164 of the retractor member 102 can be configured as a protrusion, and the engagement member 323 of the central arm 306 can be configured as a groove that is configured to receive the engagement member 323 so as to attach the refractor member 102 to the central arm 306. Alternatively, the engagement members of the retractor member 102 can be configured as grooves, and the engagement members of the central arm 306 can be configured as protrusions.

With continuing reference to FIGS. 5-6D, the engagement member 316 can include a first protrusion 320 that at least partially defines the first engagement member 321, and a second protrusion 322 that at least partially defines the second engagement member 323. The first protrusion 320 and the second protrusion 322 can protrude outward from the central arm body 308 in a direction away from the first leg 312 and the second leg 314. Specifically, each of the first clamping prong 320 and the second clamping prong 322 can protrude from the central arm body 308 generally in a forward direction indicated by arrow 324. The first protrusion 320 and the second protrusion 322 can also be referred to as clamping prongs. Furthermore, the first engagement member 321, the second engagement member 323, and the outer arm surface 309 cooperate to define an engagement opening 326 that is configured and sized to receive the engagement assembly 162 to hold the retractor member 102 (FIG. 6). The cross-section of the engagement opening 326 can be substantially dovetail shaped so that the engagement opening 326 is configured to receive the engagement assembly 162 that is dovetail shaped. The engagement opening 326 is also referred to as the substantially dovetail shaped opening.

With reference to FIGS. 4A-6D, the engagement member 316 defines a fastening indentation 330 that extends into the outer arm surface 309. The fastening indentation 330 is configured and sized to receive lock 166 so as to attach the retractor member 102 to a portion of the refractor assembly 300, such as the central arm 306. The lock 166 can be configured to releasably attach the refractor member 102 to a portion of the retractor assembly 300, such as the central arm 306. As used herein, the term "indentation" includes, but is not limited to, hole, channel, indentation, notch, depression, a slot, a groove, an opening, a cavity, a void, or any open space that is configured and sized to receive the lock 166 so as to attach the retractor member 102 to a portion of the retractor assembly 300, such as the central arm 306. The engagement member 316 further includes a retention member 332, such a detent 334, that is configured to retain the lock 166 in the fastening indentation 330 so as to attach the retractor member 102 to a portion of the retractor assembly 300, such as the central arm 306. Specifically, the retention member 332 is configured to abut the bottom surface 165 to thereby secure the lock 166 in the fastening indentation 330. The retention member 332 defines a top surface 344 and an angled surface 342 that is configured to slide along the top angled surface 169 of the lock 166 as the lock 166 is moved toward the fastening indentation 330, thereby facilitating insertion of the lock 166 in the fastening indentation 166. The angled surface 342 can be referred to as a camming surface, and can define a plane that is oriented at an oblique angle relative to a transverse direction indicated by the arrow 340. The orientation of the angled surface 342 can be complementary to the orientation of the top angled surface 169.

Figure 2A:
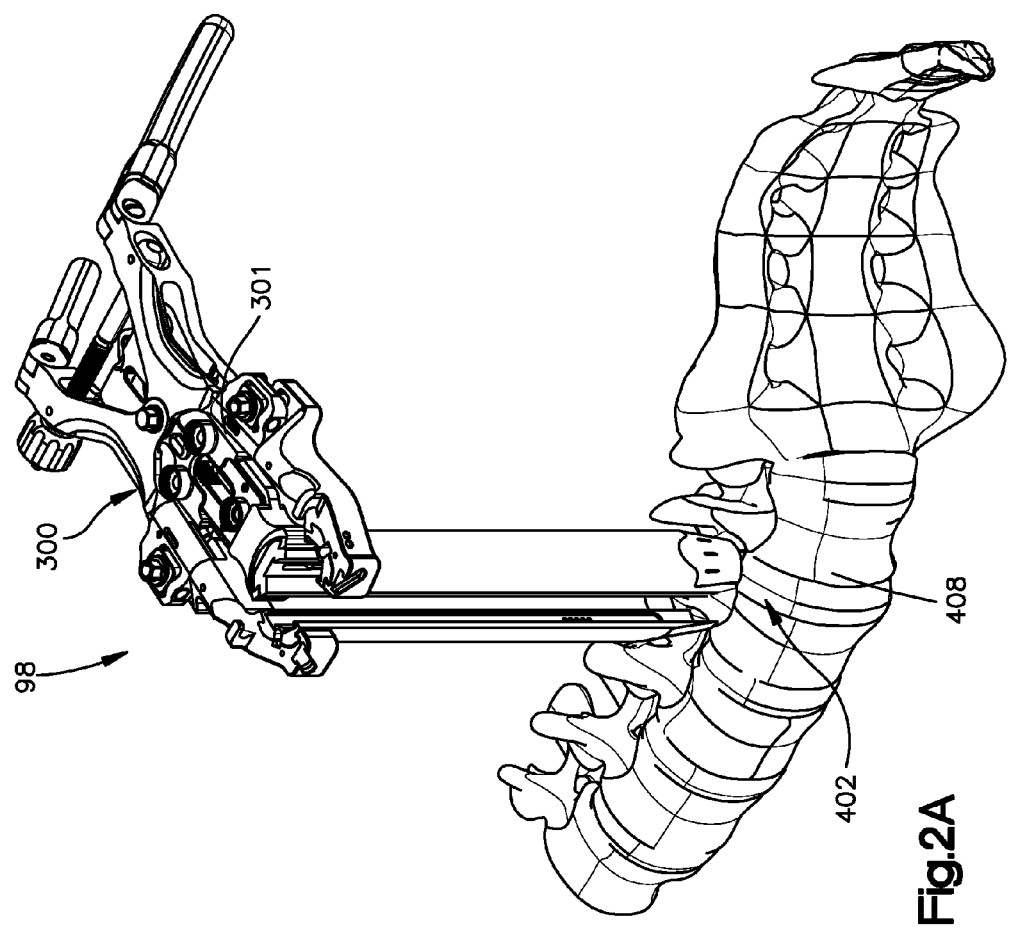
FIG. 2A is a perspective view of a retractor assembly in accordance with an embodiment of the present disclosure, including a retractor body and a plurality of retractor members extending from the body, wherein the plurality of retractor member includes the retractor member illustrated in FIG. 1 attached to the retractor body, showing the retractor assembly in a first or contracted position and disposed adjacent to the spinal column.
Figure 2B:
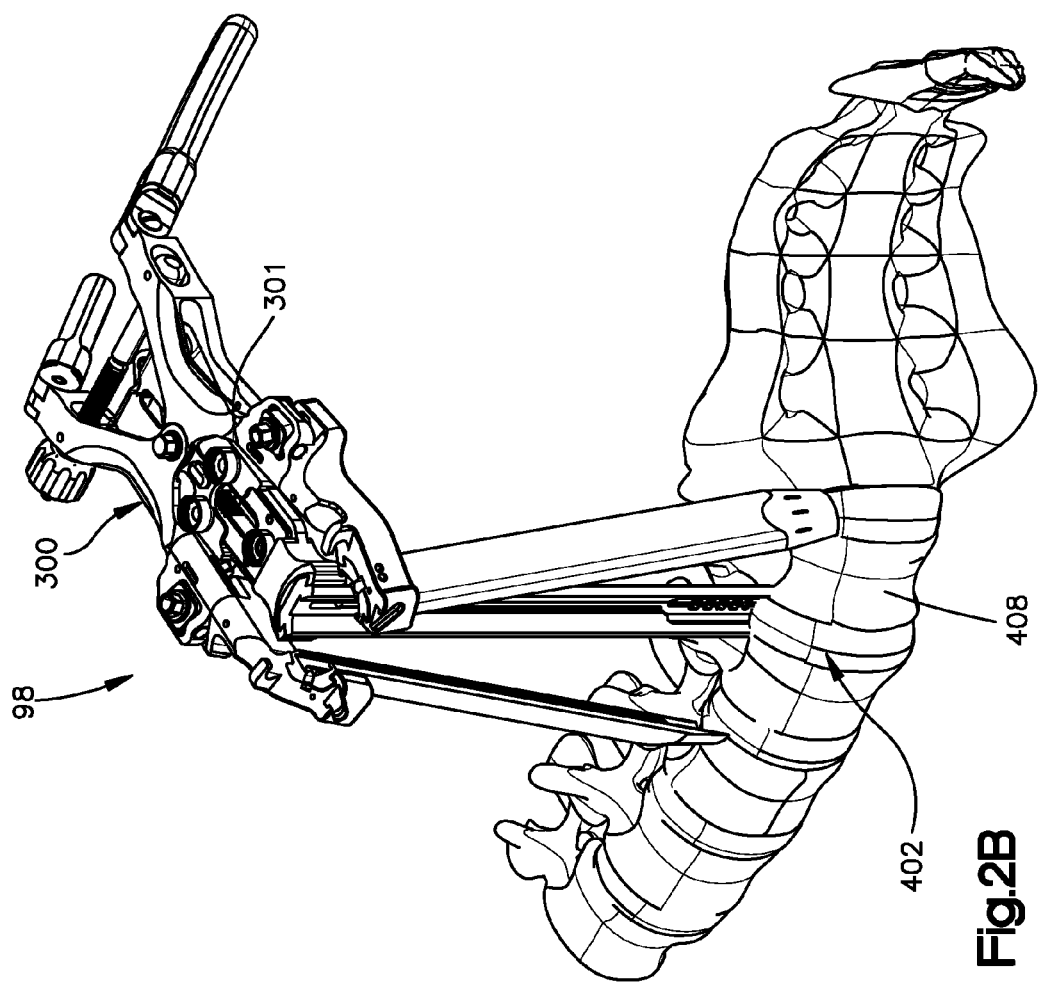
FIG. 2B is a perspective view of the retractor assembly illustrated in FIG. 2A, shown in a second or expanded position whereby the retractor members are spaced apart further than when the retractor assembly is in the contracted position.

With reference to FIGS. 4A-6D, the engagement member 316 further includes a biasing member 336, such as a spring 338, that is configured to bias the retention member 332 in the transverse direction as indicated by arrow 340. That is, the biasing member 336 can be configured to bias the retention member 332 in a direction away from the retractor body 301 (FIG. 2A). The biasing member 336 can be coupled between the retention member 332 and an inner surface 338 of the engagement member 316. Also, the biasing member 336 can be connected between the retention member 332 and central arm 306 so as to bias the retention member 332 in a direction away from the central arm 306. The retention member 332 can also be referred to as a spring-loaded retention member. The biasing member 336 is configured to bias the retention member 332 in the direction indicated by arrow 340 so that the top surface 344 is in longitudinal alignment with the bottom surface 165 of the lock 166 to secure the retractor member 102 to the central arm 306.

In operation, the central arm 306 and the retractor member 102 are moved relative to each other so that the lock 166 is advanced toward the retention member 332 until the top angled surface 169 abuts the angled surface 342. The lock 166 is then advanced toward the fastening indentation 330. As the lock 166 is advanced toward the fastening indentation 330, the angled surface 342 slides along the top angled surface 169 to facilitate insertion of the lock 166 into the fastening indentation 330. While the angled surface 342 slides along the top angled surface 169, the lock 166 urges the retention member 332 in a direction opposite to the direction indicated by arrow 340 to allow the lock 166 to be inserted into the fastening indentation 330. Upon further advancement of the lock 166 toward the fastening indentation 330, the lock 166 is no longer positioned over the retention member 332. Consequently, the biasing member 336 biases the retention member 332 in the transverse direction as indicated by arrow 340. As the retention member 332 is biased in the transverse direction, the top surface 344 of the retention member 332 contacts the bottom surface 165 of the lock 166, causing the lock 166 to be secured within the fastening indentation 330. As a consequence, the retractor member 102 is attached to the central arm 306 of the retractor assembly 300. The retractor member 102 can be releasably attached to the central arm 306 of the retractor assembly 300. In an alternative embodiment as shown in FIG. 7, the lock 166 can include an additional top surface 346 that is configured to contact an inner surface 331 that partially defines the fastening indentation 330 so as to further secure the lock 166 in the fastening indentation 330.

With reference to FIG. 8, in this embodiment, the engagement assembly 162 defines a hole 105, and the engagement member 316 includes a fastener 348 that is sized to be received in the hole 105 so as to attach the retractor member 102 to a portion of the retractor assembly 300, such as the central arm 306. It is envisioned that any portion of the retractor member 102 can define the hole 105. Thus, the retractor member 102 can define the hole 105. The fastener 348 can be configured as a screw 350, and can include a head 356 and a shaft 354 that is connected to the head 356. The shaft 354 and the head 356 can include external threads. The engagement member 316 of the central arm 306 can define an engagement opening 352 that is configured and sized to receive at least a portion of the fastener 348, such as the shaft 354. The engagement opening 352 can extend through a portion of the central arm 306 along the longitudinal direction 355. It is envisioned that any portion of the retractor assembly 300 can define the engagement opening 352. Thus, the retractor member 300 defines the engagement opening 352. In the depicted embodiment, the engagement opening 352 is configured to be aligned with the hole 105 such that the engagement opening 352 and the hole 105 are configured to collectively receive the fastener 348 to secure the first retractor member 102 to the retractor assembly 300. The engagement member 316 can further define a cavity 358 that is disposed in communication with the engagement opening 352. The cavity 358 can be configured and sized to receive at least a portion of the fastener 348, such as the head 356. The engagement assembly 162 defines a top surface 103 and the hole 105 that extends into the top surface 103 along the longitudinal direction 355. The hole 105 does not necessarily extend through the retractor member 102. Further, the hole 105 is configured and sized to receive at least a portion of the fastener 348 so as to attach the retractor member 102 to a portion of the retractor assembly 300, such as the central arm 306. For example, the hole 105 can be configured and sized to receive the shaft 354 of the fastener 348. In an embodiment, the retractor member 102 defies inner threads formed around the hole 105 that are configured to mate with external threads formed around the shaft 354 to threadedly connect the refractor member 102 to the central arm 306. The engagement assembly 162 can further include an abutment wall 360, and the engagement member 316 can define a recess 360 configured and sized to receive at least a portion of the abutment wall 199 so as to enhance the stability of the attachment between the retractor member 102 and the retractor assembly 300. The engagement member 316 can define a bottom surface 362, the recess 360 extends into the bottom surface 362. To attach the retractor member 102 to the central arm 306, the fastener 348 is inserted into the engagement opening 352 and the hole 105.

With reference to FIGS. 9A-12B illustrate a method of accessing the surgical site 402, such as the lumbar spine 408, in accordance with an embodiment of the present disclosure. The surgical site 402 can be an intervertebral disc 410 that is disposed between two vertebral bodies 412. As seen in FIGS. 9A and 9B, an obturator 500 and a second dilator 502 can be used in this method of accessing the surgical site 402. The obturator 500 defines a cross-sectional dimension D1, such as a diameter, and is elongate along a longitudinal direction 503. The second dilator 502 defines a cross-sectional dimension D1, such as a diameter. The second dilator 502 defines a cross-sectional dimension D2, such as a diameter, and is elongate along the longitudinal direction 503. The cross-sectional dimension D2 of the second dilator 502 is greater than the cross-sectional dimension D1 of the obturator 500. The second dilator 502 defines a first dilator hole 504, such as a bore, that is elongate along the longitudinal direction 503. The first dilator hole 504 is configured and sized to receive the obturator 500.

Before inserting at least one of the obturator 500 or the second dilator 502, a sensor 501 can be used to detect the position of nerves in the tissue body 400. For example, the sensor 501, which can be a neuromonitoring probe, can be inserted laterally and advanced toward the surgical site 402 until its tip 505 is inserted into the surgical site 402. As illustrated in FIGS. 9A and 9B, the obturator 500 is inserted into the tissue body 400. The sensor 501 can also be a triggered electromyography (tEMG) probe. Alternatively, reference number 501 can represent a wire such as a Kirschner wire. Next, the obturator 500 is advanced toward the desired surgical site 402 to dilate the portion of the tissue body 400 leading to the surgical site 402. Instead of (or in addition to) the obturator 500, a Kirschner wire can be inserted through the tissue body 400, and then advanced toward the surgical site 402. The second dilator 502 is then positioned over the obturator 500, and then inserted into the tissue body 400. The obturator 500 serves as a guide for the second dilator 502. The second dilator 502 is then advanced toward the surgical site 402 to dilate the portion of the tissue body 400 leading toward the surgical site 402. It is envisioned that more than one dilator of increasing cross-sectional dimensions can be used to dilate at least a portion of the tissue body 400 in a sequential fashion.

With reference to FIGS. 10A and 10B, the dilator assembly 100 defines a cross-sectional dimension D3, such as a diameter. The cross-sectional dimension D3 of the dilator assembly 100 is greater than the cross-sectional dimension D2 of the second dilator 502. After inserting the second dilator 502 into the tissue body 400, the dilator assembly 100 is placed over the second dilator 502, and advanced toward the surgical site 402 to further dilate the portion of the tissue body 402 leading toward the surgical site 402. During insertion, the dilator assembly 100 can dilate, for example, the psoas muscle. While inserting the dilator assembly 100, the user should avoid contacting, impinging, or damaging nerves by using, for example, the sensors as discussed above. Then, the second dilator 502 and the obturator 500 are removed from the tissue body 400. The dilator 106 is also removed from the tissue body 400 by detaching the dilator 106 from the retractor member 102. To do so, the dilator 106 can be moved in a direction away from the surgical site 402. That is, the dilator 106 is moved in a direction indicated by arrow 506 so that the first engagement member 154 slides along the engagement member 156, and the engagement member 158 slides along the engagement member 160 until the dilator 106 is detached from the retractor member 102.

With reference to FIGS. 11A and 11B, after the dilator 106, the obturator 500, and the second dilator 502 are removed from the tissue body 400, the retractor member 102 is left in its original position. An arm can be used to fix the position of the retractor member 102 in the tissue body 400. The arm can be connected to an operating table or any other suitable fixed structure. In addition (or alternatively), the retractor member 102 can be anchored to intervertebral disc 410 using, for example, the shim 141.

With reference to FIGS. 12A and 12B, at least a portion of the retractor assembly 300 is then inserted in the space dilated by the dilator assembly 100 along the direction indicated by arrow 508. Specifically, the cranial retractor member 370 and the caudal retractor member 372 of the retractor assembly 330 are inserted in the space of the tissue body 400 that was dilated by the dilator assembly 100. Also, the central arm 306 of the retractor assembly 300 is advanced toward the retractor member 102 that is disposed in the tissue body 400. In particular, the central arm 306 of the retractor assembly 300 is advanced along the direction indicated by arrow 508 until at least a portion of the central arm 306 contacts the retractor member 102. The central arm 306 can be connected to the retractor member 102 as described in detail above. At this point, the cranial retractor member 370, the caudal retractor member 372, and the posterior retractor member 102 collectively establish a passageway toward the surgical site 402. Then, the retractor assembly 300 can be actuated to move the retractor member 102, the cranial retractor member 370, and the caudal retractor member 372 relative to one another in order to change the size of the passageway.

In one embodiment, the method of accessing the surgical site can include the following steps inserting a dilator assembly into a tissue body, the dilator assembly comprising a dilator and a refractor member removably attached to the dilator; advancing the dilator assembly toward the surgical site to dilate at least a portion of the tissue body; detaching the dilator from the retractor member; removing the dilator from the tissue body while leaving the refractor member in the tissue body; and attaching a retractor assembly to the retractor member disposed in the tissue body.

FIGS. 13A-14B illustrate several steps of a method of accessing the surgical site 402 in accordance with an alternative embodiment of the present disclosure. In this method, the obturator 500, the second dilator 502, and the dilator assembly 100 are inserted into the tissue body 400, and advanced toward the desired surgical site 402 as described and illustrated above. Then, the obturator 500, the second dilator 502, and the dilator assembly 100 remain in the tissue body 400. That is, the obturator 500, the second dilator 502, and the dilator assembly 100 are not removed from the tissue body 400. Next, the cranial retractor member 370 and the caudal retractor member 372 of the retractor assembly 330 are placed over the dilator assembly 100. Specifically, the cranial retractor member 370 and the caudal retractor member 372 are placed over the dilator 106, and advanced toward the desired surgical site 402 in the direction indicated by arrow 508. The central arm 306 is also advanced toward the desired surgical site until the central arm 306 contacts the retractor member 102. Then, central arm 306 can be connected to the refractor member 102 as described in detail above.

With reference to FIGS. 14A and 14B, once the central arm 306 is connected to the posterior retractor member 102, the obturator 500 and the second dilator 502 can be removed from the tissue body 400. To do so, the obturator 500 and the second dilator 502 can be moved away from the desired surgical site in the direction indicated by arrow 509. The dilator 106 is also removed from the tissue body 400. To do so, the dilator 106 can be moved in a direction away from the surgical site 402. That is, the dilator 106 is moved in a direction indicated by arrow 509 so that the engagement member 154 slides along the engagement member 156, and the engagement member 158 slides along the engagement member 160 until the dilator 106 is detached from the refractor member 102. After the obturator 500, the second dilator 502, and the dilator 106 have been removed from the tissue body 400, the cranial retractor member 370, the caudal retractor member 372, and the posterior retractor member 102 collectively establish a passageway toward the surgical site 402. Then, the retractor assembly 300 can be actuated to move the retractor member 102, the cranial retractor member 370, and the caudal retractor member 372 relative to one another in order to change the size of the passageway.

In one embodiment, the method of accessing the surgical site 400 includes the following steps: inserting a dilator assembly into a tissue body, the dilator assembly comprising a dilator and a refractor member removably attached to the dilator; advancing the dilator assembly toward the surgical site to dilate at least a portion of the tissue body; removing the dilator from the tissue body while leaving the retractor member in the tissue body; and attaching a retractor assembly to the retractor member disposed in the tissue body. The step of attaching the retractor assembly to the retractor member can be performed after the step of removing the dilator from the tissue body. The step of attaching the retractor assembly to the retractor member can be performed before the step of removing the dilator from the tissue body. The dilator can be referred to as the first dilator, and the method can further include the step of advancing a second dilator toward the surgical site to dilate at least a portion of the tissue body. The step of advancing the dilator assembly toward the surgical site can include moving the dilator assembly over the second dilator so that the dilator assembly at least partially surrounds the second dilator. The method can further include advancing an obturator toward the surgical site, wherein the step of advancing the second dilator toward the surgical site includes moving the second dilator over the obturator such that at least a portion of the second dilator surrounds at least a portion of the obturator.

Figure 15A:
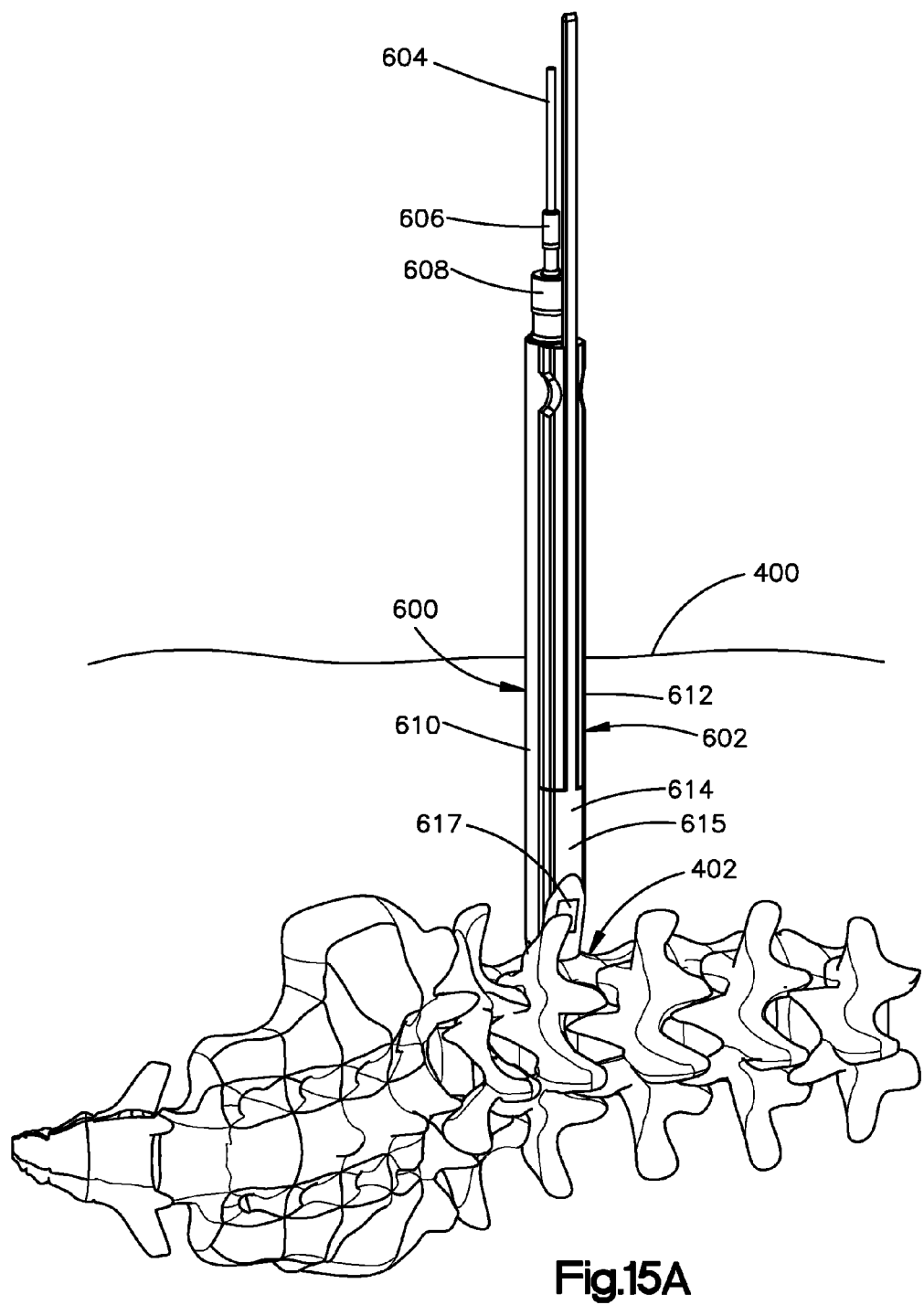
FIG. 15A is a perspective view of a dilator assembly constructed in accordance with an embodiment of the present disclosure, including a Kirschner wire, a first dilator, a second dilator, and a neuromonitoring device, showing the dilator assembly disposed adjacent to a spinal column.
Figure 15B:
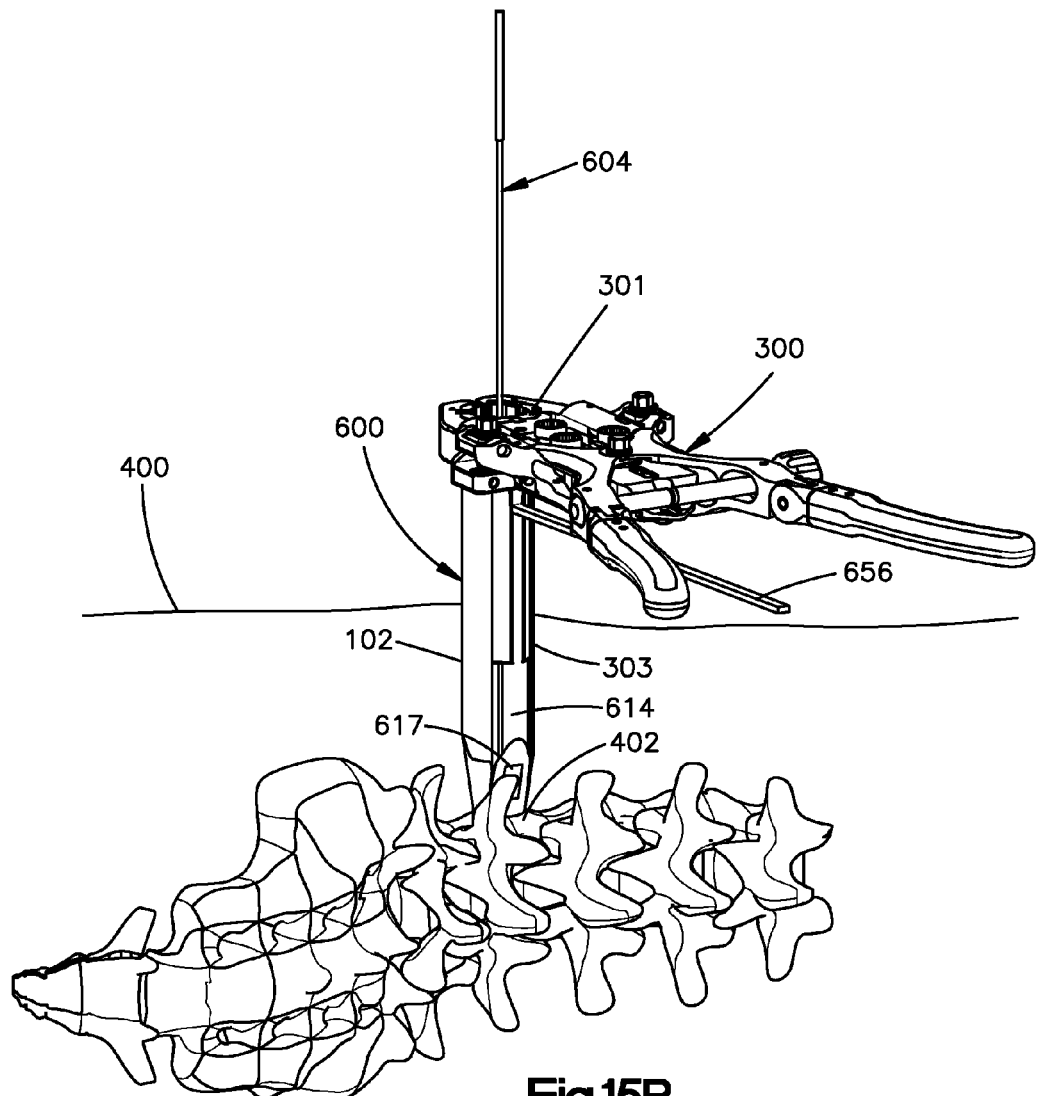
FIG. 15B is a perspective view of the retractor assembly shown in FIG. 2A connected to a portion of the dilator assembly of FIG. 15A.
Figure 16A:
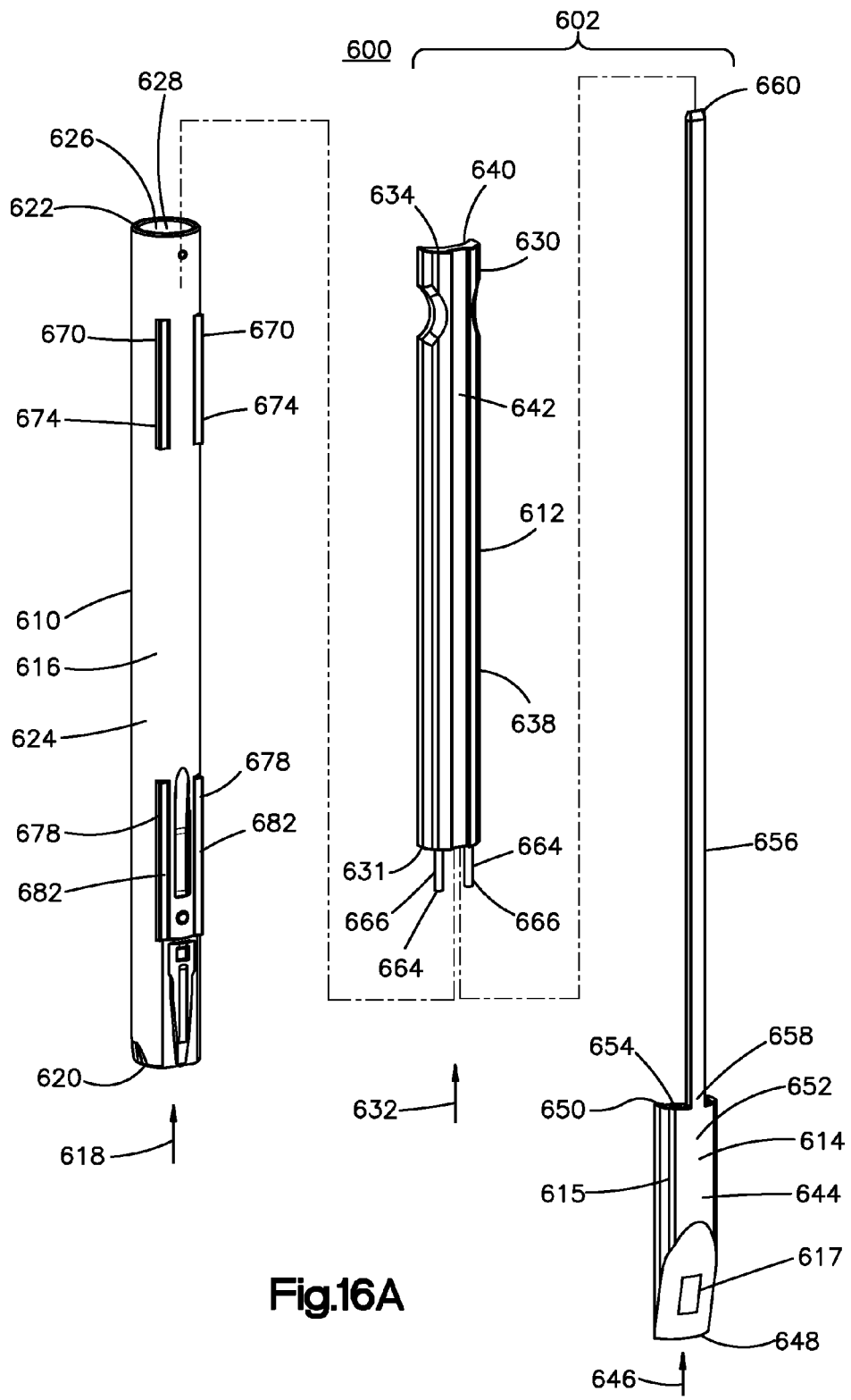
FIG. 16A is a perspective exploded view of a portion of the dilator assembly shown in FIG. 15A.

With reference to FIGS. 15A-15B, the tissue retraction system 98 can include the retractor assembly 300 and a dilator assembly 600 in accordance with an alternative embodiment of the present disclosure. The dilator assembly 600 can be configured to be inserted to be inserted into a tissue body 400 so as to at least partially define a passageway toward the desired surgical site 402. The dilator assembly 600 can include one or more wires 604, such as Kirschner wires, a neuromonitoring device 602, and a plurality of dilators. In particular, the dilator assembly 600 can include a first dilator 606, a second dilator 608, and a third dilator 610. The third dilator 610 and the neuromonitoring device 602 can cooperate so as to define a passageway toward the surgical site 402. The first dilator, the second dilator 608, and the third dilator 610 can each have substantially tubular shape. Alternatively, the first dilator, the second dilator 608, and the third dilator 610 can each have substantially partial tubular shape. For example, the first dilator, the second dilator 608, and the third dilator 610 can each define one or more slots.

The neuromonitoring device 602 can include a first portion 612 and a second portion 614 both of which can be removed from the third dilator 610. The first portion 612 can also be referred to as the proximal portion, and the second portion 614 can be referred to as the distal portion. The first portion 612 can be partly or entirely made of a reusable or disposable material. For instance, the first portion 612 can partly or entirely made of aluminum, polyetheretherketone (PEEK), stainless steel or any other suitable material. The first portion 612 and the second portion 614 can be connected to each other to define the neuromonitoring device 602. The second portion 614 can be configured as a neuromonitoring member 615 that is configured to detect properties or characteristics of the tissue body 400. For instance, the neuromonitoring member 615 can be used for electromyography (EMG), mechanomyogram (MMG), pressure sensing, vibration sensing, or a combination thereof. The neuromonitoring device 602 can thereby provide output to a user interface so as to provide guidance information to a user that can be used to guide the dilator assembly 600 without impinging upon nerve tissue. The neuromonitoring device 602 can be removed from the third dilator 606.

With reference to FIGS. 16A-16D, the dilator assembly 600 can include the third dilator 606, which can also be referred to as the dilator, and the first portion 612 and the second portion 614 of the neuromonitoring device 602. The dilator 606 can have a substantially cylindrical shape and can include a dilator body 616 that is elongate along a longitudinal direction 618. Alternatively, the dilator 606 can define a substantially partial cylindrical shape. The dilator body 616 can define a first dilator end 620 and a second dilator end 622 that is spaced from the first dilator end 620 along the longitudinal direction 618. The first dilator end 620 can be configured as a proximal dilator end, while the second dilator end 622 can be configured as a distal dilator end. The dilator body 616 defines an outer dilator surface 624 and an opposed inner dilator surface 626. The inner dilator surface 626 can define a dilator opening 628 that is elongate along the longitudinal direction 618. The dilator opening 628 can extend through the dilator body 616 from the first dilator end 620 to the second dilator end 622. Furthermore, the dilator opening 628 can be configured and sized to receive another dilator, such as the second dilator 608. To this end, the dilator opening 628 can define a cross-sectional dimension D4. The cross-section dimension D4 can be a diameter. The dilator 616 can be connected to the first portion 612 and the second portion 614 as discussed in detail below.

With continuing reference to FIGS. 16A-D, the first portion 612 can be configured as a retractor member, such as a refractor blade, and includes a body 630. In particular, the first portion 612 can be constructed as a posterior retractor blade. The body 630 of the first portion 612 can be elongate along a longitudinal direction 632, and can define a first retractor end 634 and a second retractor end 636 that is spaced from the first retractor end 634 along the longitudinal direction 632. The first retractor end 634 can be configured as a proximal end, while the second retractor end 636 can be configured as a distal end. The body 630 can define an outer surface 638 and an opposed inner surface 640. The first portion 612 can further define a recess 642, such as a groove, that extends into the outer surface 638. The recess 642 can be elongate along the longitudinal direction 632. Moreover, the recess 642 can extend from the first end 631 to the second retractor end 634 of the body 630. The recess 642 can be configured and sized to receive at least a portion of the second portion 614.

With continuing reference to FIGS. 16A-D, as discussed above, the second portion 614 can be configured as a neuromonitoring member 615 that is configured to sense to detect properties or characteristics of the tissue body 400. For instance, the neuromonitoring member 615 can be used for electromyography (EMG), mechanomyogram (MMG), pressure sensing, and/or vibration sensing. In an embodiment, the neuromonitoring member 615 can include one or more electrodes 617 that are configured to detect properties or characteristic of the tissue body. For example, the electrode 617 can monitor the direction, pathology, and proximity of nerves. The electrode 617 can be attached to a surface of the neuromonitoring member 615. Alternatively, the electrode 617 and associated electrical wiring can be embedded in the neuromonitoring member 615. For instance, the electrode 617 and the associated electrical wiring can be embedded in the neuromonitoring member 615 during molding. The neuromonitoring member 615 can be configured to be electrically coupled to an electrical power source.

With continuing reference to FIGS. 16A-D, the second portion 614 includes a body 644 that is elongate along a longitudinal direction 646, and can define a first end 648 and a second end 650 that is spaced from the first end 648 along the longitudinal direction 646. The body 644 of the second portion 614 can further define an outer surface 652 and an opposed inner surface 654. The electrode 617 can be attached to the outer surface 652 of the body. Alternatively, the electrode 617 can be attached to the inner surface 654 of the body 644. In another embodiment, the electrode 617 can be embedded in the body 644 as discussed above.

With continuing reference to FIGS. 16A-D, the second portion 614 can further include an electrical connection member 656, such as wires or a bar, that protrudes from the body 644. The electrical connection member 656 can transmit electrical energy to the electrode 617 stemming from an electrical power source. Thus, the electrical connection member 656 can be partly or entirely made of an electrically conductive material. In the depicted embodiment, the electrical connection member 656 protrudes from the second end 650 of the body 644 along the longitudinal direction 646. The electrical connection member 656 can be elongate along the longitudinal direction 646, and can be configured and sized to be received in the recess 642 of the first portion 612. In particular, the electrical connection member 656 can define a first end 658 that is attached to the body 644 and a second end 660 that can be electrically coupled to an electrical power source via any suitable electrical connection such as a wiring. The first end 658 can be spaced from the second end 660 along the longitudinal direction 646. The electrical connection member 656 can be bent.

With continuing reference to FIGS. 16A-D, the second portion 614 can be connected to the first portion 612 via any suitable connection, such as a snap fit connection. The first portion 612 can include one or more first engagement members 664, and the second portion 614 can include one or more second engagement members 662 that are configured to mate with the first engagement members 664 so as to couple the first portion 612 to the second portion 614. In the depicted embodiment, the first engagement members 662 can be configured as protrusions 666, such as pins, that protrude from the body 630 of the first portion 612. Specifically, the protrusions 666 can protrude from the first end 631 of the body 630 in the longitudinal direction 632. The protrusions 666 can have a substantially cylindrical shape, and can be elongate along the longitudinal direction 666. The second engagement members 662 can be configured as openings 668 that extend into the body 644. Specifically, the openings 668 can extend into the second end 650 of the body 644. Each of the openings 668 is configured to receive a protrusion 666 so as to couple the first portion 612 to the second portion 614. Thus, when the protrusions 666 are inserted into the respective openings 668, the protrusions 666 and openings 668 define a snap fit connection that is configured to secure the first portion 612 to the second portion 614.

With continuing reference to FIGS. 16A-D, as discussed above, the first portion 612 can be connected to the third dilator 610. In the depicted embodiment, the first portion 612 can include one or more engagement members 670, and the second portion 614 can include one or more engagement members 672 that are configured to mate with respective engagement members 670 so as to couple the first portion 612 to the second portion 614. The engagement members 670 can be configured as protrusions 674 that protrude from the outer dilator surface 624 of the dilator body 616. The protrusions 674 can be configured as rails, and can define a substantially triangular cross-section. In the depicted embodiment, the protrusions 674 can be elongate along the longitudinal direction 618, and are disposed closer to the second dilator end 622 than to the first dilator end 620. The engagement members 672 of the first portion 612 can be configured as one or more recesses 676 each configured to securely receive a protrusion 674 so as to couple the first portion 612 to the dilator 610. The insertion of the protrusions 674 in the respective recesses 676 causes a friction fit connection between the dilator 610 and the first portion 612. To connect the dilator 610 to the first portion 612, the first portion 612 can be moved along the outer dilator surface 624 in a direction toward the first dilator end 622 (i.e., the direction opposite to the longitudinal direction 618) such that the protrusions 674 are positioned in the recesses 676. Once a significant portion of each protrusions 674 is disposed in the respective recess 676, the protrusions 674 frictionally fit within the recesses 676 so as to prevent, or at least inhibit, the first portion 612 from moving farther along the direction toward the first dilator end 620. To decouple the first portion 612 from the dilator 610, the first portion 612 can be moved along the outer dilator surface 624 in the longitudinal direction 618 until the protrusions 674 are no longer disposed in the recesses 676.

With continuing reference to FIGS. 16A-D, as discussed above, the second portion 614 can be connected to the third dilator 610. In the depicted embodiment, the dilator 610 can include one or more engagement members 678, and the second portion 614 can include one or more engagement members 680 that are configured to mate with the engagement members 678 so as to couple the dilator 610 to the second portion B14. The engagement members 678 can be configured as protrusions 682 that protrude from the outer dilator surface 624 of the dilator body 616. The protrusions 682 can be configured as rails, and can define a substantially triangular cross-section. In the depicted embodiment, the protrusions 682 can be elongate along the longitudinal direction 618, and are disposed closer to the first dilator end 620 than to the second dilator end 622. The engagement members 680 can be configured as recesses 684 each of which is configured and sized to securely receive a respective protrusion 682 so as to couple the second portion 614 to the dilator 610. The insertion of the protrusions 682 in the respective recesses 684 causes a friction fit connection between the dilator 610 and the second portion 614. To connect the dilator 610 to the second portion 614, the second portion 614 can be moved along the outer dilator surface 624 in a direction toward the first dilator end 622 (i.e., the direction opposite to the longitudinal direction 618) such that the protrusions 682 are positioned in the recesses 684. Once a significant portion of each protrusion 682 is disposed in the respective recess 684, the protrusions 682 frictionally fit within the recess 684 so as to prevent, or at least inhibit, the second portion 614 from moving farther along the direction toward the first dilator end 620. To decouple the second portion 614 from the dilator 610, the second portion 614 can be moved along the outer dilator surface 624 in the longitudinal direction 618 until the protrusions are no longer disposed in the recesses 684.

Figure 17A:
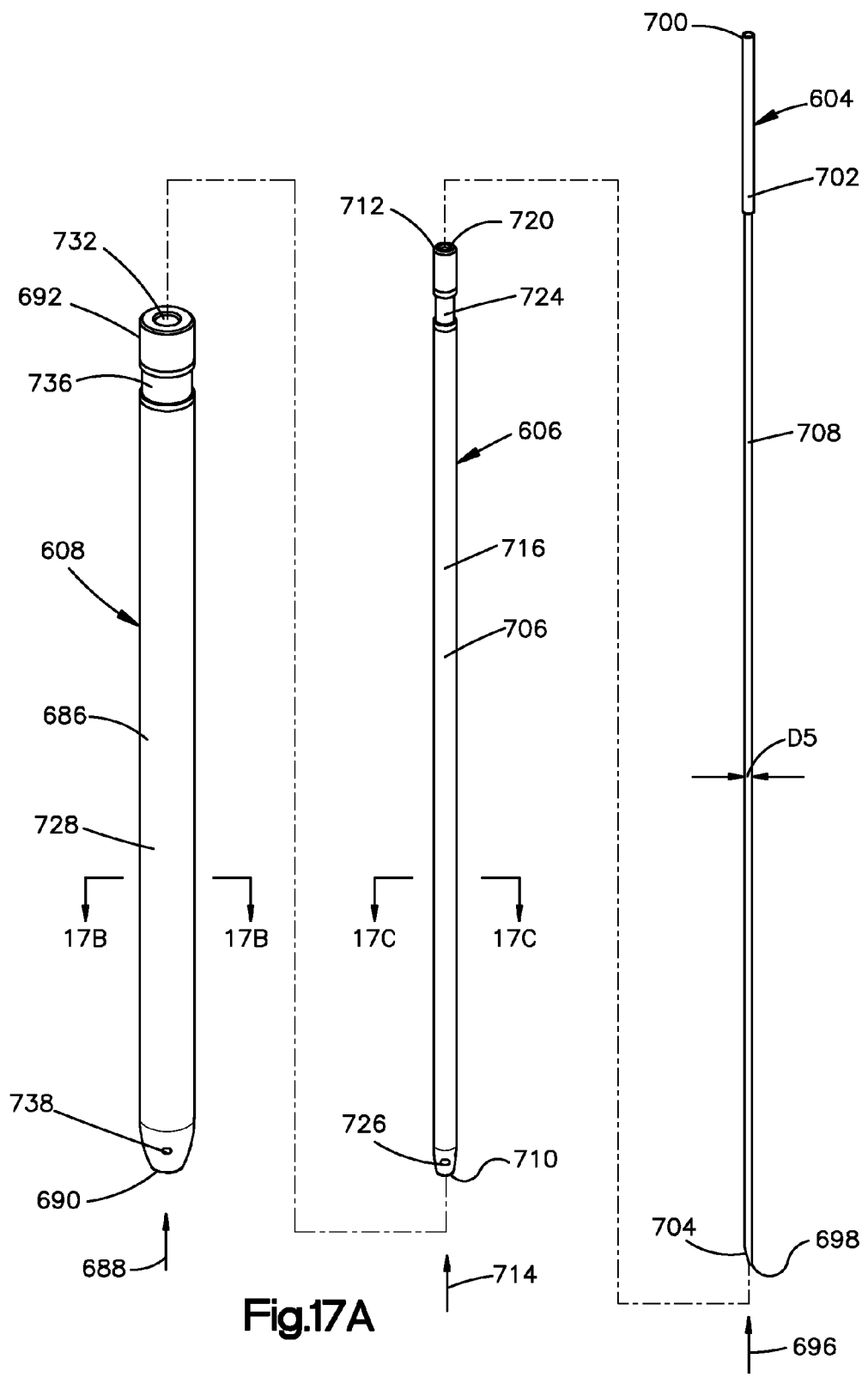
FIG. 17A is an exploded view of the wire, the first dilator, and the second dilator shown in FIG. 15A.
Figure 17C:
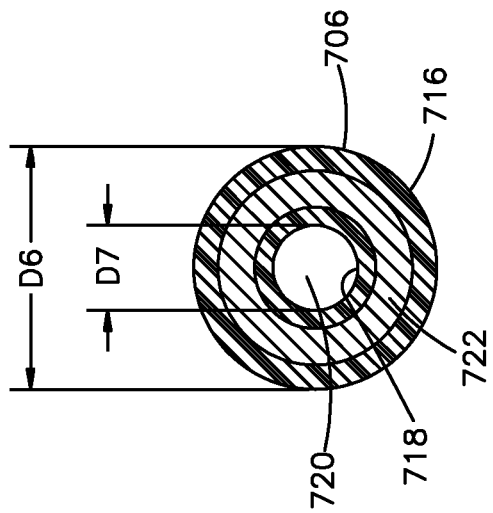
FIG. 17C is a top cross-sectional view of the first dilator shown in FIG. 17A, taken along section line 17C-17C.
Figure 17B:
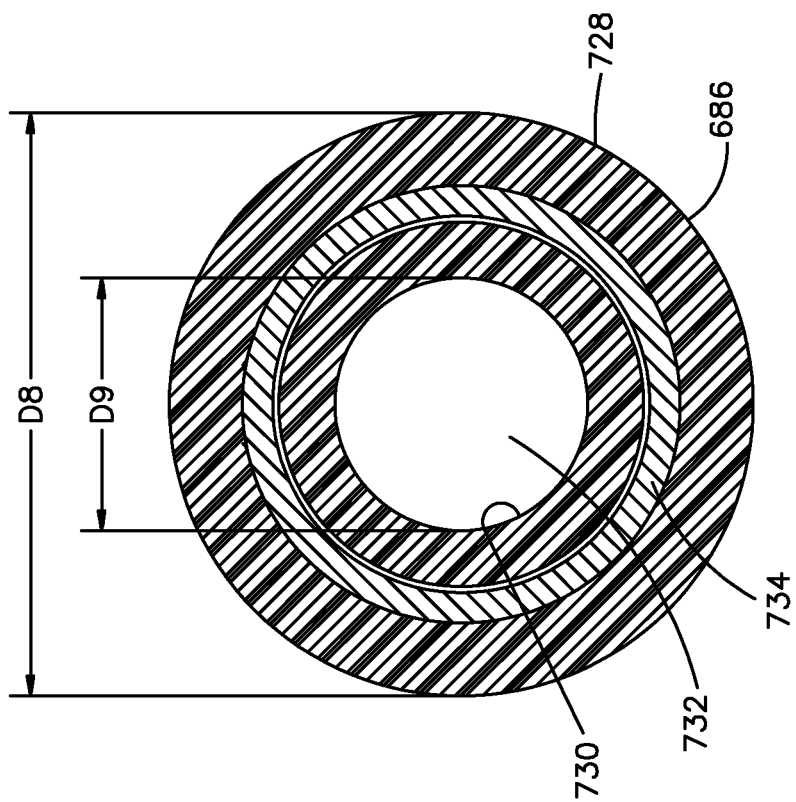
FIG. 17B is a top cross-sectional view of the second dilator shown in FIG. 17A, taken along section line 17B-17B.

With reference to FIGS. 17A-C, the dilator assembly 600 can further include the first dilator 606, the second dilator 608, the third dilator 610, and the wire 604 as discussed above. Each of the first dilator 606, the second dilator 608, and the third dilator 610 is configured to dilate the tissue body 400. The wire 604 can be configured to secure to the target surgical site 402, and can guide the movement of the dilators 606, 608, and 610 toward the surgical site 402.

With continuing reference to FIGS. 17A-C, the wire 604 can be configured as a Kirschner wire (also known as K-wire) and can be elongate along a longitudinal direction 696. The wire 606 can define a first wire end 698 and a second wire end 700 that is spaced from the first wire end 698 along the longitudinal direction 696. The wire 604 can include a handle 702 that is located closer to the second wire end 700 than to the first wire end 698, and can be configured to be grasped by a user in order to facilitate manipulation of the wire by that user. The wire 604 can include a pointed tip 704 that is configured to be inserted through the tissue body 400 and into the surgical site 402. The pointed tip 704 can be located at the first wire end 698, and can have a substantially tapered configuration. In addition, the pointed tip 704 can be configured to be inserted in the intervertebral disc annulus to secure the wire 604 to the surgical site 402. Moreover, the wire 604 can define an outer wire surface 708 that in turn defines a cross-sectional dimension D5, such as a diameter.

With continuing reference to FIGS. 17A-C, the first dilator 606 can include a dilator body 706 that defines a first dilator end 710 and a second dilator end 712 that is spaced from the first dilator end 710 along a longitudinal direction 714. The dilator body 706 can be elongate along the longitudinal direction 714, and can be configured to dilate the tissue body 400. The dilator body 706 can define an outer dilator surface 716 and an opposed inner dilator surface 718. The outer dilator surface 716 can define a cross-sectional dimension D6, such as a diameter. The inner dilator surface 718 can define a dilator opening 720 that extends through the dilator body 706. The dilator opening 720 can be elongated along the longitudinal direction 714, and can define a cross-sectional dimension D7, such as a diameter. In the depicted embodiment, the dilator opening 720 can be configured and sized to slidably receive the wire 604. Thus, the cross-sectional dimension D7 can be greater than or at least substantially similar to the cross-sectional dimension D5. The first dilator 606 can further include an electrically conductive member 722 that is at least partially disposed between the dilator outer surface 716 and the dilator inner surface 718. The dilator outer surface 716, the dilator inner surface 718, or both can be partly or entirely made of an electrical insulating material. On the other hand, the electrically conductive member 722 can be partly or entirely made of an electrically conductive material. The electrically conductive member 722 can thus be configured to transmit electrical energy, and can include an exposed portion 724 that is not covered by the dilator outer surface 716. The exposed portion 724 can be located closer to the second dilator end 712 than to the first dilator end 710, and allows the electrically conductive member 720 to be connected to neuromonitoring apparatus or system, such as an EMG clip. Thus, the exposed portion 724 can be electrically connected to a neuromonitoring apparatus or system. The first dilator 606 can further include an electrode 726 that is electrically coupled to the electrically conductive member 722. The electrode 726 can be configured to detect properties or characteristics of the tissue body 400. In use, the electrode 726 can be used for electromyography (EMG), mechanomyogram (MMG), pressure sensing, and/or vibration sensing. The electrode 726 can therefore provide output to a user interface so as to provide guidance information to a user that can be used to guide the dilator 606 without impinging upon nerve tissue. For instance, the electrode 726 can be configured to monitor the direction, pathology, and proximity of nerves.

With continuing reference to FIGS. 17A-C, the second dilator 608 can include a dilator body 686 that is elongate along a longitudinal direction 688. The dilator body 686 can define a first dilator end 690 and a second dilator end 692 that is spaced from the first dilator end 690 along the longitudinal direction 688. The dilator body 686 can define an outer dilator surface 728 and an opposed inner dilator surface 730. The outer dilator surface 728 can define a cross-sectional dimension D8, such as a diameter. The inner dilator surface 730 can define a dilator opening 732 that in turn defines a cross-sectional dimension D9, such as a diameter. The dilator opening 732 can be configured and sized to slidably receive the first dilator 606. Thus, the cross-sectional dimension D9 is greater or at least substantially similar to the cross-sectional dimension D6. The dilator opening 732 can extend through the dilator body 686 and can be elongate along the longitudinal direction 688. Furthermore, the second dilator 608 can include an electrically conductive member 734 that is at least partially disposed between the outer dilator surface 728 and the inner dilator surface 730. The electrically conductive member 734 can be configured to transmit electrical energy, and can be partly or entirely made of an electrically conductive material. On the other hand, the outer dilator surface 728, the inner dilator surface 730, or both can be partly or entirely made of an electrically insulating material. The electrically conductive member 734 can include an exposed portion 736 that is not covered by the outer dilator surface 728. The exposed portion 736 can be located closer to the second dilator end 692 than to the first dilator end 690, and allows the electrically conductive member 732 to be connected to neuromonitoring apparatus or system, such as an EMG clip. Thus, the exposed portion 736 can be electrically connected to a neuromonitoring apparatus or system. The second dilator 608 can further include an electrode 738 that is electrically couple to the electrically conductive member 732. The electrode 738 can be configured to detect properties or characteristics of the tissue body 400. In use, the electrode 738 can be used for electromyography (EMG), mechanomyogram (MMG), pressure sensing, and/or vibration sensing. The electrode 738 can therefore provide output to a user interface so as to provide guidance information to a user that can be used to guide the dilator 606 without impinging upon nerve tissue. For instance, the electrode 738 can be configured to monitor the direction, pathology, and proximity of nerves.

With reference again to FIGS. 15A-B, the tissue retraction system 98 can be configured to dilate and retract the tissue body 400 to establish a passageway toward the surgical site 402. In an embodiment, the tissue retraction system 98 can include the dilator assembly 600 and the retractor assembly 300. The dilator assembly 600 can be configured to dilate the tissue body 400 to establish a passageway toward the surgical site 402. Various method and procedures can be employed to dilate and retract the tissue body 400 with the tissue retraction system 98. For example, the wire 604 can be inserted into the tissue body 400 and advanced toward the desired surgical site 402. The advancement of the wire 604 into the tissue body 400 and toward the surgical site 402 can be guided using fluoroscopy or any other suitable imaging technique. The wire 604 can be inserted into the tissue body 400 and advanced toward the surgical site 402 until the pointed tip 704 is inserted in an intervertebral disc annulus to thereby anchor the wire 604 to the patient. The insertion of the wire 604 into the tissue body 402 can cause dilation of the tissue body 400.

Next, the first dilator 606 can be advanced over the wire 604 and toward the surgical site 402. To this end, the first dilator 606 can be positioned over the wire 604 such that the wire 604 is disposed in the dilator opening 720. During insertion of the first dilator 606 into the tissue body 400, the electrode 726 of the first dilator 606 can monitor properties or characteristics of the tissue body 400 as discussed above. For example, the electrode 726 can monitor the direction, pathology, and proximity of nerves. The electrode 726 can continue to detect the properties or characteristics of the tissue body 400 even after the first dilator 606 has been placed in the desired position.

Then, the first dilator 606 can be advanced into the tissue body 400 and toward the surgical site 402 in order to dilate the tissue body 400 from an initial position to a first dilated position. Then, the second dilator 608 can be advanced over the first dilator 606 and toward the surgical site 402 to further dilate the tissue body 400. For instance, the second dilator 608 can be positioned over the first dilator 606 such that the first dilator 606 is disposed in the dilator opening 732. Then, the second dilator 608 can be advanced into the tissue body 400 and toward the surgical site 402 in order to dilate the tissue body 400 from the first dilated position to the second dilated position. During insertion of the second dilator 608 into the tissue body 400, the electrode 738 of the second dilator 608 can monitor properties or characteristics of the tissue body 400 as discussed above. For example, the electrode 738 can monitor the direction, pathology, and proximity of nerves. The electrode 732 can continue to detect the properties or characteristics of the tissue body 400 even after the second dilator 608 has been placed in the desired position.

Next, the third dilator 610 that is pre-connected to the neuromonitoring device 602 can be advanced into the tissue body 400 and toward the surgical site 402. Specifically, the pre-connected third dilator 610 and neuromonitoring device 602 can be positioned over the second dilator 608 such that the second dilator 608 is disposed in the dilator opening 628. Then, the pre-connected third dilator 610 and neuromonitoring device 602 can be advanced over the second dilator 608 so that neuromonitoring device 602 faces the posterior side of the patient. The third dilator 610 can be advanced over the second dilator 608 so that the During insertion of the-connected third dilator 610 and neuromonitoring device 602 into the tissue body 400, the electrode 617 can monitor properties or characteristics of the tissue body 400 as discussed above. The electrode 617 can continue to detect the properties or characteristics of the tissue body 400 even after the neuromonitoring device 602 has been placed in the desired position.

Once the dilator assembly 600 has been positioned in the desired location in the tissue body 400, the first portion 612 of the neuromonitoring device 602 can be decouple from the third dilator 610 and removed from the tissue body 400, while leaving the second portion 614 in the tissue body 400. The second portion 614 can be anchored to the surgical site, such as the intervertebral disc annulus, using a shim that slidably coupled to the second portion 614. The insertion of the shim to a portion of the tissue body 400, such as the disc annulus, facilitates securement and stabilization of the second portion 614 before insertion of the retractor members 102 into the tissue body 400. The secure and stabilization of the second portion 614 in the tissue body 400 also prevents, or at least minimizes, tissue encroachment from the posterior side of the second portion 614 because the second portion 614 is pre-positioned and secured before the retractor members 102 are introduced into the tissue body 400. If necessary or desired, the first dilator 606, the second dilator 608, and the wire 604 can be removed from the tissue body 400. Alternatively, the first dilator 606 and the second dilator 608 can be removed from the tissue body 400 while leaving the wire 604 in the tissue body 400. Also, the first dilator 606, the second dilator 608, the third dilator 610, and the wire 604 can be removed from the tissue body 400 while leaving only the second portion 614 in the tissue body 400. Also, the first dilator 606, the second dilator 608, and the third dilator 610 can be removed from the tissue body 400 while leaving the wire 604. Regardless of which components are removed from the tissue body 400 at this juncture of the process, the second portion 614 can remain in the tissue body 400. Before connecting the retractor assembly 300 to the second portion 614, the electrical connection member 656 can be bent to avoid interference with the retractor assembly 300.

Then, the retractor assembly 300 is advanced toward the tissue body 400 so that the retractor members 102 are advanced toward the surgical site 402. For instance, the retractor members 102 can be advanced toward the surgical site 402 such that the retractor members 102 are disposed around the wire 604, the third dilator 610, or both. While the retractor members 102 are advanced into the tissue body 400 and toward the surgical site 402, the partial retractor member 303 can be connected to the second section 614 as discussed above. Then, if necessary, the first dilator 606, the second dilator 608, the third dilator 610, the wire 604, or a combination thereof, can be removed from the tissue body 400, while leaving the second portion 614 neuromonitoring device 602 in the tissue body 400. As discussed above, the electrode 617 of the second portion 614 can detect properties or characteristics of the tissue body 400. For instance, the electrode 617 can monitor the direction, pathology, and proximity of nerves.

The use of the dilator assembly 600 and associated methods as describe above allow continuous neuromonitoring of the tissue body 400 during advancement of the retractor members 102 into the tissue body 400, because the second portion 614, which contains an electrode 617, remains in the tissue body 400 during insertion of the retractor members 102 into the tissue body. It is envisioned that the retractor members 102 can be constructed as the partial retractor 303, and therefore can be attached to other second portions 614 that have neuromonitoring capabilities as described above.

With reference to FIGS. 18A-G, the retractor assembly 300 can include the partial retractor member 303 that is configured to be coupled to the second portion 614. The partial retractor member 303 can cooperate with the second portion 614 so as to form a complete retractor member 102, which can be constructed as a posterior retractor member. In an embodiment where the second portion is configured as the neuromonitoring member 615, the retractor member 800 can be configured to be coupled to the neuromonitoring member 615 so as to couple the retractor assembly 300 to the neuromonitoring member 615. The partial retractor member 303 can cooperate with the neuromonitoring member 615 so as to form a complete retractor member, which can be constructed as a posterior retractor member.

With continuing reference to FIGS. 18A-G, the partial retractor member 303 can include a body 305 and at least one engagement assembly 162 that is carried by the body 305. The engagement assembly 162 can be substantially similar or identical to the engagement assembly 162 described above in connection with FIGS. 4A-F above. The partial retractor assembly 303 can be coupled to the retractor body 301 via the engagement assembly 162 as described above. The body 305 defines an outer surface 364 and an opposed inner surface 366. Further, the partial retractor member 303 can define a recess 368, such as a groove that extends into the outer surface 364. The recess 368 can be elongate along a longitudinal direction 370, and can be configured and sized to receive at least a portion of the neuromonitoring member 615 such as a portion of the electrical connection member 656.

With continuing reference to FIGS. 18A-G, the partial retractor member 303 can further include one or more engagement members 374 that are each configured to engage a respective engagement member 670 of the dilator 610 so as to guide the movement of the partial retractor member 303 along the dilator 610 when the partial retractor member 303 is being moved toward the neuromonitoring member 615 along the dilator 610. The engagement members 374 can be configured as recesses 376 that are each configured to receive a respective protrusion 674 of the dilator 610.

With continuing reference to FIGS. 18A-G, the partial retractor member 303 can further include a first engagement member 376, a second engagement member 378, and a fourth engagement member 380. The first engagement member 376 can be configured to mate the engagement member 662 of the neuromonitoring member 615 so as to couple the partial retractor member 303 to the neuromonitoring member 615. For example, the first engagement member 378 can be configured as a protrusion 382, such a pin, that protrudes from the body 305 along the longitudinal direction 370. The protrusion 382 can be configured and sized to be securely received in one of the openings 668 of the neuromonitoring member 615 so as to couple the partial retractor member 303 to the neuromonitoring member 615. The second engagement member 378 can be configured to mate a respective engagement member 662 of the neuromonitoring member 615 so as to couple the partial retractor member 303 to the neuromonitoring member 615. For example, the second engagement member 378 can be configured as a protrusion 384, such as a pin, that protrudes from the body 305 along the longitudinal direction 370. The protrusion 384 can be configured and sized to be securely received in one of the openings 668 of the neuromonitoring member 615 so as to couple the partial retractor member 303 to the neuromonitoring member 615. The third engagement member 380 can be configured as a latch 386, which can be hook-shaped. The latch 380 is configured to engage the neuromonitoring member 615 through an opening 661 of the neuromonitoring member 615 so as to couple the partial retractor member 303 to the neuromonitoring member 615.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A tissue retraction system configured to dilate a tissue body, the tissue retraction system comprising:
   a dilator configured to be inserted into the tissue body toward a surgical site, the dilator including a dilator body that is elongate along a respective longitudinal direction and sized to dilate the tissue body, the dilator body defining a proximal end and a distal end that is spaced from the proximal end along the respective longitudinal direction, and the dilator body terminates at first and second dilator sides that extend between the proximal and distal ends, the dilator further including at least one engagement member that is recessed along at least one of the dilator sides;
   a first retractor member that includes a body that is elongate along the respective longitudinal direction and at least one engagement member that is configured to attach to the at least one engagement member of the dilator so as to removably attach the first retractor member to the dilator body along the respective longitudinal direction, the first retractor member and the dilator cooperate so as to define a passageway when the first retractor member is attached to the dilator body, wherein one of the at least one engagement members of the dilator and the first retractor member defines a protrusion that is elongate along the respective longitudinal direction and the other of the at least one engagement members of the dilator and the first retractor member defines a groove that is elongate along the respective longitudinal direction and receives the protrusion so as to removably attach the first retractor member to the dilator; and
   a retractor assembly including a retractor body and at least a second retractor member that is movably supported by the retractor body, the retractor body configured to be attached to the first retractor member, wherein the retractor body is configured so as to cause the second retractor member to splay away from the first retractor member when the first retractor member is attached to the retractor body.

2. The tissue retraction system as recited in claim 1, wherein the engagement members of the dilator and the first retractor member attach such that the first retractor member is movable with respect to the dilator along the respective longitudinal direction.

3. The tissue retraction system as recited in claim 1, wherein the passageway is enclosed along all directions that are substantially perpendicular to the longitudinal direction.

4. The tissue retraction system as recited in claim 1, wherein the body of the first retractor member defines a proximal end and a distal end that is spaced from the proximal end along the longitudinal direction, the body of the first retractor member terminates at first and second retractor sides that extend between the proximal and distal ends of the body of the first retractor member, and the at least one engagement member of the first retractor member extends out of least one of the retractor sides.

5. The tissue retraction system as recited in claim 1, wherein the dilator defines first and second protrusions, and the first retractor member defines first and second grooves that are configured to receive the first and second protrusions.

6. The tissue retraction system as recited in claim 1, wherein the first retractor member includes an engagement assembly that is configured to secure the body of the first retractor member to the retractor assembly.

7. The tissue retraction system as recited in claim 6, wherein the retractor assembly defines an engagement opening that is configured to receive the engagement assembly to secure the first retractor member to the retractor assembly.

8. The tissue retraction system as recited in claim 7, wherein the retractor assembly includes a retention member that is configured to retain the engagement assembly in the engagement opening so as to secure the first retractor member to the retractor assembly.

9. The tissue retraction system as recited in claim 8, wherein the retractor assembly includes a biasing member that is configured to bias the retention member in a direction away from the retractor body.

10. The tissue refraction system as recited in claim 1, further comprising a fastener that is configured to connect the first retractor member to the retractor assembly.

11. The tissue retraction system as recited in claim 10, wherein the first retractor member defines a hole, and the retractor assembly defines an engagement opening that is configured to be aligned with the hole such that the engagement opening and the hole are configured to collectively receive the fastener to secure the first retractor member to the retractor assembly.

12. The tissue retraction system as recited in claim 1, further comprising
 a neuromonitoring member configured to detect at least one property of the tissue body, the neuromonitoring member configured to be coupled to the dilator.

13. The tissue retraction system as recited in claim 12, wherein the dilator body defines an outer dilator surface, and the neuromonitoring member is configured to be coupled along the outer dilator surface.

14. The tissue retraction system as recited in claim 12, wherein the neuromonitoring member includes at least one electrode that is configured to detect at least one property of the tissue body.

15. The tissue retraction system as recited in claim 14, wherein the neuromonitoring member includes at least one electrical connection member that is configured to transmit electrical energy to the electrode from an electrical power source.

16. A tissue retraction system configured to dilate a tissue body, the tissue retraction system comprising:
 a dilator configured to be inserted into the tissue body toward a surgical site, the dilator including a dilator body that is elongate along a respective longitudinal direction and sized to dilate the tissue body, the dilator further including at least one engagement member;
 a first retractor member that includes a body that is elongate along the respective longitudinal direction, at least one engagement member that is configured to attach to the at least one engagement member of the dilator so as to removably attach the first retractor member to the dilator body, wherein the first retractor member and the dilator cooperate so as to define a passageway when the first retractor member is attached to the dilator body, the first retractor member including an engagement assembly; and
 a retractor assembly including a retractor body, an engagement opening that is configured to receive the engagement assembly, a retention member that is configured to retain the engagement assembly in the engagement opening so as to secure the first retractor member to the retractor assembly, and a biasing member that is configured to bias the retention member in a direction away from the retractor body, the retractor assembly further including at least a second retractor member that is movably supported by the retractor body such that the second retractor member is moveable away the first retractor member when the first retractor member is secured to retractor assembly.

17. The tissue retraction system as recited in claim 16, wherein the engagement members of the dilator and the first retractor member attach such that the first retractor member is movable with respect to the dilator along the respective longitudinal direction.

18. The tissue retraction system as recited in claim 16, wherein the passageway is enclosed along all directions that are substantially perpendicular to the longitudinal direction.

19. The tissue retraction system as recited in claim 16, wherein one of the at least one engagement members of the dilator and the first retractor member defines a protrusion that is elongate along the respective longitudinal direction, and the other of the at least one engagement members of the dilator and the first retractor member defines a groove that is elongate along the respective the longitudinal direction and receives the protrusion so as to removably attach the first retractor member to the dilator.

20. The tissue retraction system as recited in claim 16, wherein the dilator body defines a proximal end and a distal end that is spaced from the proximal end along the longitudinal direction, the dilator body terminates at first and second dilator sides that extend between the proximal and distal ends, and the at least one engagement member of the dilator is recessed in at least one of the dilator sides.

\* \* \* \* \*